(12) United States Patent
Wang et al.

(10) Patent No.: US 11,478,437 B2
(45) Date of Patent: Oct. 25, 2022

(54) FORMULATIONS FOR HAIR GROWTH

(71) Applicant: JENIVISION INC., Irvine, CA (US)

(72) Inventors: Weizhen Wang, Irvine, CA (US);
David F. Woodward, Lake Forest, CA (US)

(73) Assignee: JENIVISION INC., Irvine, CA (US)

(*) Notice: Subject to any disclaimer, the term of this patent is extended or adjusted under 35 U.S.C. 154(b) by 722 days.

(21) Appl. No.: 16/626,248

(22) PCT Filed: Jun. 30, 2017

(86) PCT No.: PCT/US2017/040453
§ 371 (c)(1),
(2) Date: Dec. 23, 2019

(87) PCT Pub. No.: WO2019/005139
PCT Pub. Date: Jan. 3, 2019

(65) Prior Publication Data
US 2020/0215007 A1   Jul. 9, 2020
US 2022/0031638 A9   Feb. 3, 2022

(30) Foreign Application Priority Data
Jul. 5, 2016 (CN) .......................... 201610525215.4

(51) Int. Cl.
| A61K 31/16 | (2006.01) |
| A61K 47/44 | (2017.01) |
| A61K 47/10 | (2017.01) |
| A61P 17/14 | (2006.01) |
| A61K 9/00  | (2006.01) |

(52) U.S. Cl.
CPC ............ *A61K 31/16* (2013.01); *A61K 9/0014* (2013.01); *A61K 47/10* (2013.01); *A61K 47/44* (2013.01); *A61P 17/14* (2018.01)

(58) Field of Classification Search
CPC ...... A61K 31/16; A61K 9/0014; A61K 47/10; A61K 47/44; A61P 17/14
USPC .......................................................... 514/563
See application file for complete search history.

(56) References Cited

U.S. PATENT DOCUMENTS

| 5,510,383 A    | 4/1996  | Bishop et al.   |
| 6,626,105 B1   | 9/2003  | Linehan         |
| 8,227,514 B2   | 7/2012  | Rethore et al.  |
| 8,865,766 B2   | 10/2014 | Woodward et al. |
| 9,597,328 B2*  | 3/2017  | Jain ........................ A61P 27/04 |
| 2007/0160562 A1 | 7/2007  | Brinkenhoff    |
| 2008/0275118 A1 | 11/2008 | Shaw et al.    |
| 2011/0124725 A1 | 5/2011  | Maskin         |
| 2012/0129789 A1 | 5/2012  | Yoelin         |
| 2012/0251613 A1 | 10/2012 | Jain et al.    |
| 2013/0266674 A1 | 10/2013 | Hall           |
| 2014/0322148 A1 | 10/2014 | Jackson        |
| 2015/0025097 A1 | 1/2015  | Hu et al.      |
| 2015/0328108 A1 | 11/2015 | Trogden et al. |
| 2015/0328109 A1 | 11/2015 | Arezki et al.  |
| 2016/0136071 A1 | 5/2016  | Corboy, Jr.    |
| 2017/0049734 A1 | 2/2017  | Woodward et al.|
| 2022/0031638 A9 | 2/2022  | Wang et al.    |

FOREIGN PATENT DOCUMENTS

| CN | 105263469 A      | 1/2016  |
| EP | 2498783 A2       | 9/2012  |
| JP | 2016512246 A     | 4/2016  |
| KR | 20150030971 A    | 3/2015  |
| WO | WO-0074519 A2    | 12/2000 |
| WO | WO-2007078861 A2 | 7/2007  |
| WO | WO-2009136439 A1 | 11/2009 |
| WO | WO-2010065487 A1 | 6/2010  |
| WO | WO-2011057129 A2 | 5/2011  |
| WO | WO-2011113855 A2 | 9/2011  |
| WO | WO-2012038469 A2 | 3/2012  |
| WO | WO-2012065065 A1 | 5/2012  |
| WO | WO-2014070784 A1 | 5/2014  |
| WO | WO-2014158373 A1 | 10/2014 |
| WO | WO-2014191969 A1 | 12/2014 |

OTHER PUBLICATIONS

Chinese Application No. 201610525215.4 First Office Action and English Translation dated Jul. 21, 2020.
Emer M.D.: Novel Treatment of Female-Pattern Androgenetic Alopecia With Injected Bimatroprost 0.03% Solution. Journal of Drugs IN20111231 Dermatology. 10(7):795-798 (2011).
PCT/US2017/040453 International Preliminary Report on Patentability dated Dec. 31, 2019.
PCT/US2017/040453 International Search Report and Written Opinion dated Sep. 25, 2017.
Chinese Application No. 201610525215.4 Second Office Action dated Dec. 7, 2020.

(Continued)

*Primary Examiner* — Kristin A Vajda
(74) *Attorney, Agent, or Firm* — Wilson Sonsini Goodrich & Rosati

(57) ABSTRACT

The present invention is directed to compositions and formulations for hair growth. The non-aqueous, preservative-free formulations are useful for the growth of hair, eyebrows and eyelash in a variety of setting. Also provided herein are non-aqueous, preservative-free formulations and methods for the treatment of dry-eye and related symptoms.

18 Claims, 4 Drawing Sheets

(56) References Cited

OTHER PUBLICATIONS

Great Britain Patent Application No. GB2000837.1 Office Action dated Nov. 11, 2021.
Japanese Application No. 2019-571530 Reason for Refusal dated Jun. 13, 2021.
Korean Patent Application No. 10-2020-7002957 Office Action dated Sep. 1, 2021.
Lee et al., Hair growth-promoting effects of lavender oil in C57BL/6 mice. Toxicol Res. 32(2):103-108(2016).
Oh et al., Peppermint oil promotes hair growth without toxic signs. Toxicol Res. 30(4):297-304 (2014).

* cited by examiner

Application device.

Bacterial and fungal growth testing of Formulation 3, Table 1 as described in Example I.

Results of the growth of right eyelash and left and right eyebrows using Formulation 13, Table 2 as described in Example III.

Results of the growth of right eyelash using Formulation 13, Table 2 as described in Example IV.

FORMULATIONS FOR HAIR GROWTH

CROSS REFERENCE

This application is a U.S. National Phase of International Application No. PCT/US2017/040453 filed on Jun. 30, 2017.

FIELD OF THE INVENTION

The present invention is directed generally to compositions and formulations for hair growth. The present invention is directed specifically to non-aqueous hair, eyebrows and eyelash growth formulations of active eicosanoids which do not contain preservatives.

SUMMARY OF THE INVENTION

Non-aqueous formulations and methods for formulating hair growth promoting eicosanoids are described such that the chemical stability of eicosanoids and their pro-drugs is improved and the use of preservatives is not necessary in the formulation. Although it is optional, a bulk packing hair growth product may contain preservatives to prolong the shelf life once opened for daily use. Such non-aqueous formulations are composed of ingredients that occur naturally. These formulations may be delivered by methods and devices that conserve usage and are convenient to the patient. Of notable utility is a positive displacement cylindrical device fitted with a felt/fiber tip or a specialized brush for direct application to the eyelid margin. Such a delivery method results in reduced risk of applying drug to unwanted areas such as the eyeball and conjunctiva. Further, the addition of natural hair shaft and hair follicle health promoting and appearance enhancing essential and plant oils are included in the formulations.

One aspect of the present invention includes a method for treating alopecia or hair loss and/or an attribute associated with hair loss, such as hair thinning, hair color loss, no new hair shaft growth, reduced rate of hair shaft growth, reduced hair shaft diameter (thickness), reduced hair shaft length, reduced hair density, reduced hair pigmentation, reduced melanin production, decreased keratinization of the hair shaft, reduced hair shaft luster, reduced hair health, increased fragility of the hair shaft, reduced time a hair follicle spends in anagen phase, reduced time a hair follicle spends in catagen phase, reduced time a hair follicle spends in telogen phase, premature release of hair shaft from hair follicle in exogen phase, premature initiation of apoptosis in hair follicle, premature conversion of a terminal hair into a vellus hair, failure of vellus hair to convert to terminal hair.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Terms and Definitions

Figure 1:
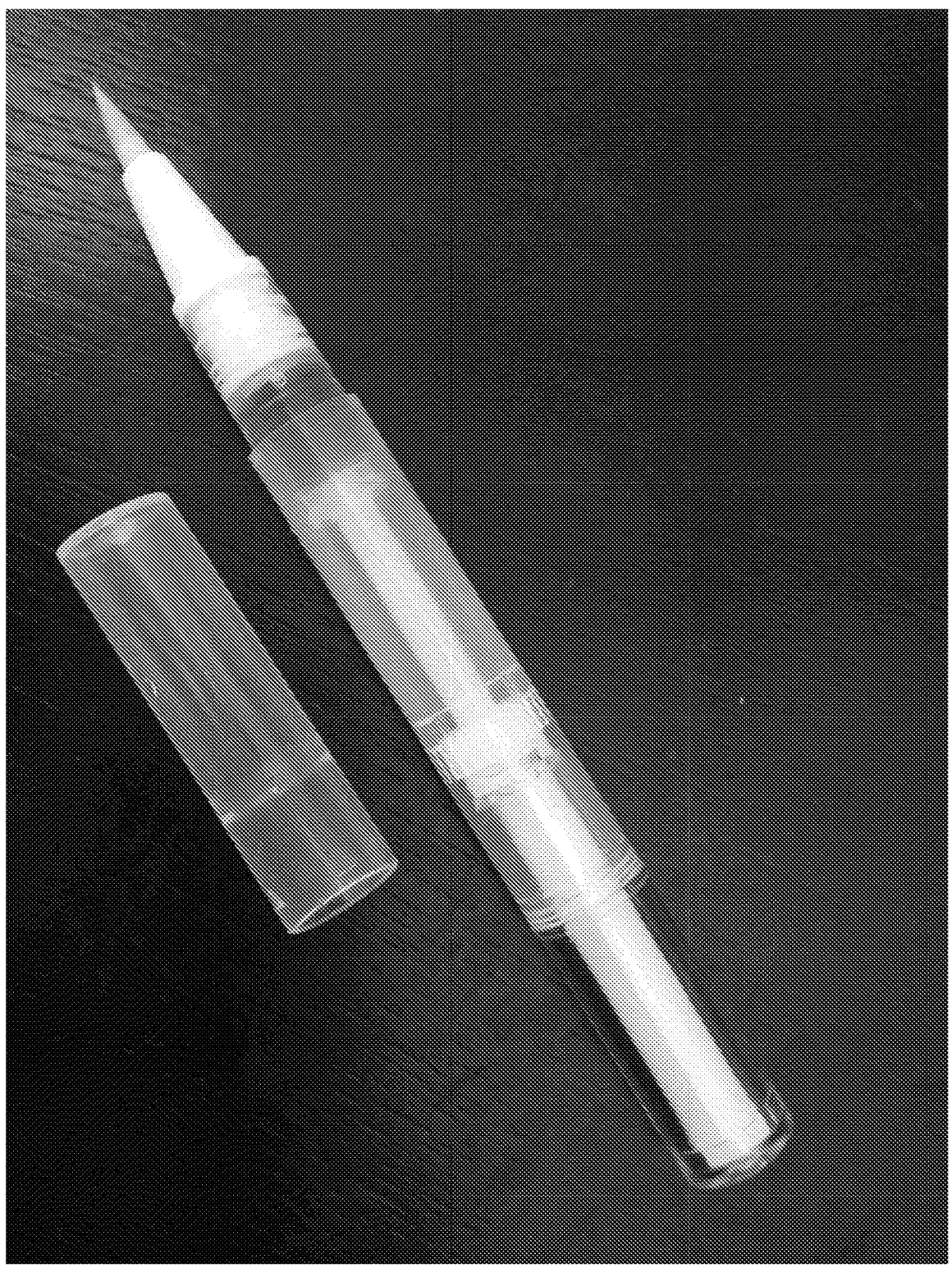
FIG. 1 shows one embodiment of an applicator device.

The terms "about", "approximate" and "approximately" are used herein to modify a numerical value and indicate a defined range around that value. If "x" were the value, "about x" or "approximately equal to x" would generally indicate a value from 0.90x to 1.10x. Any reference to "about x" minimally indicates at least the values x, 0.90x, 0.91x, 0.92x, 0.93x, 0.94x, 0.95x, 0.96x, 0.97x, 0.98x, 0.99x, 1.01x, 1.02x, 1.03x, 1.04x, 1.05x, 1.06x, 1.07x, 1.08x, 1.09x, and 1.10x. Thus, "about x" is intended to disclose, e.g., "0.98x." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." About may also refer to a number close to the cited number that would result in a bioequivalent therapeutic effect by a regulatory agency such as the FDA or the EMEA.

The term "alcohol" refers to an alkyl substituted with at least one hydroxy substituent. The alkyl can be substituted with one, two, three, four, five, or six hydroxy substituents. In certain embodiments, an alcohol comprises one to fifteen carbon atoms (e.g., $C_1$-$C_{15}$ alcohol). In certain embodiments, an alcohol comprises one to ten carbon atoms (e.g., $C_1$-$C_{10}$ alcohol). In certain embodiments, an alcohol comprises one to eight carbon atoms (e.g., $C_1$-$C_8$ alcohol). In certain embodiments, an alcohol comprises one to six carbon atoms (e.g., $C_1$-$C_6$ alcohol). In certain embodiments, an alcohol comprises one to three carbon atoms (e.g., $C_1$-$C_3$ alcohol).

The term "Alkyl" refers to a straight or branched hydrocarbon chain radical consisting solely of carbon and hydrogen atoms, optionally containing unsaturation, having from one to twenty six carbon atoms (e.g., $C_1$-$C_{26}$ alkyl)). In certain embodiments, an alkyl comprises one to twenty four carbon atoms (e.g., $C_1$-$C_{24}$ alkyl). In certain embodiments, an alkyl comprises one to twenty two carbon atoms (e.g., $C_1$-$C_{22}$ alkyl). In certain embodiments, an alkyl comprises one to twenty carbon atoms (e.g., $C_1$-$C_{20}$ alkyl). In certain embodiments, an alkyl comprises one to eighteen carbon atoms (e.g., $C_1$-$C_{18}$ alkyl). In certain embodiments, an alkyl comprises one to sixteen carbon atoms (e.g., $C_1$-$C_{16}$ alkyl). In certain embodiments, an alkyl comprises one to ten carbon atoms (e.g., $C_1$-$C_{10}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl).

In some embodiments the alcohol is a $C_{5-20}$ alkanol. In some embodiments the alcohol is a $C_{5-20}$ alkanol is a diol. In some embodiments the alcohol is a $C_{5-20}$ alkanol is a triol. In some embodiments the alcohol is a $C_{5-20}$ alkanol wherein the alkane portion of the alkanol is branched. In some embodiments the $C_{5-20}$ alkanol is saturated. In some embodiments the $C_{5-20}$ alkanol is unsaturated.

"Alopecia" is defined as hair loss and includes hypotrichosis of the eyelashes or loss of hair from eyebrows and may include different types of alopecia including but not limited to alopecia areata, scarring alopecia, non-scarring alopecia, androgenetic alopecia, telogen effluvium, trichotillomania, alopecia universalis, androgenic alopecia and alopecia totalis, transient alopecia areata, diffuse pattern alopecia.

The term "eicosanoid" refers to a signaling molecule made by the oxidation of arachidonic acid or other polyunsaturated fatty acids. Eicosanoids are 20 carbon units in length. Examples of eicosanoids include prostanoids, leukotrienes, lipoxins, resolvins, and eoxins.

The term "prostanoid" refers to physiologically active lipid compounds derived from fatty acids. Many prostanoids act as vasodilators and inhibit the aggregation of blood platelets. Examples of prostanoids include prostaglandin $F_{2\alpha}$, dinoprost, latanoprost, bimatoprost, travoprost, carboprost, tafluprost, and thromboxane.

The term "prostamide" refers to physiologically active lipids derived from fatty acid amides, notably anandamide. These are known to lower intraocular pressure, reduce fat deposits, and increase hair growth. Examples include bimatoprost, and prostamides $F_{2\alpha}$, $E_2$, and $D_2$.

The term "leukotriene" refers a family of eicosanoid inflammatory mediators produced in leukocytes by the oxidation of arachidonic acid and the essential fatty acid eicosapentaenoic acid. Examples of leukotriene include leukotriene $C_4$, leukotriene $D_4$, leukotriene $E_4$, leukotriene $F_4$, leukotriene $B_4$, leukotriene G4, and leukotriene B5.

The term "lipoxin" refers to bioactive autacoid metabolites of arachidonic acid. Lipoxins often play important roles in inflammatory responses. Examples of lipoxins include lipoxin lipoxin $B_4$, 15-epi-lipoxin $A_4$, and 15-epi-lipoxin B4.

The term "resolvin" refers to autacoid metabolites of arachidonic acid. Many resolvins have been seen to possess anti-inflammation, tissue protection, and tissue healing activities. Examples of resolvins include resolvin Ds, resolvin Es, resolvin Dn-6DPA, and resolvin Dn-3DPA.

The term "eoxin" refers to a family of proinflammatory that are produced in human eosinophils and mast cells through the metabolism of arachidonic acid. Many eoxins contribute to inflammation in airway allergies and certain types of cancers. Examples of eoxins include eoxin $A_4$, eoxin $C_4$, eoxin $D_4$, and eoxin $E_4$.

The term "glyceride" refer to esters formed from glycerol and at least one fatty acid. The term glyceride is meant to include monoglycerides, diglycerides and triglycerides. Many vegetable and animal oils contain triglycerides.

The term "preservative" refers to a chemical that prevents, slows or inhibits the decomposition of a formulation. In some instances, a preservative prevents decomposition of the active ingredient by preventing, slowing or inhibiting decomposition by microbial or chemical interaction. Non-limiting examples of a preservative include benzalkonium chloride (BAK), purite, benzododecinium bromide, ionic buffered systems, polixetonium, sodium perborate, polyhexamethylene biguanide, polyquad, GenAqua, and sofZia. The term preservatives is also meant to encompass stabilizers such as perborate, boric acid and ethylenediaminetetraacetic acid (EDTA).

"Hypotrichosis" is a condition of abnormal hair loss or reduction.

"Non-aqueous formulations" are formulations that contain no water.

"Plant oils" refer to oils derived from plant sources. There are three primary types of plant oil, differing both the means of extracting the relevant parts of the plant, and in the nature of the resulting oil: (1) Vegetable oils historically extracted by putting part of the plant under pressure, squeezing out the oil; (2) Macerated oils consisting of a base oil to which parts of plants are added; and, (3) Essential oils composed of volatile aromatic compounds, extracted from plants by distillation.

The term "oil" as used in the formulations described herein refers to a liquid or semi-solid hydrophobic substance derived from a plant, animal or petrochemical source.

In some embodiments, the oil may be derived from almond, argan, avocado, beech nut, blackcurrant seed, brazil nut, butternut squash seed, *camellia* (tea seed), cape chestnut, cashew nut, castor, cocoa butter, coconut, corn, cottonseed, flaxseed, grape seed, hazelnut, hemp seed, jojoba, kapok seed, kenaf seed, okra seed, olive, palm, peanut, pomegranate seed, poppy seed, soybean, sunflower seed or any combinations thereof.

In some embodiments, the oil may be derived from angelica root, balsam of Peru, basil, camphor, cannabis flower, cardamom, carrot seed, cedarwood, chamomile, calamus, cinnamon, cistus, citron, citronella, clary sage, clove, coriander, costus root, cranberry seed, cumin, cypress, davana, elecampane, eucalyptus, fennel seed, frankincense, galangal, galbanum, geranium, goldenrod, grapefruit seed, henna, helichrysum, hickory nut, Idaho tansy, jasmine, juniper berry, *Laurus nobilis*, lavender, ledum, lemongrass, mandarin, menthe arvensis, moringa, mountain savory, mugwort, myrrh, neroli, nutmeg, parsley, patchouli, perilla, pennyroyal, petitgrain, red cedar, rose, rosehip, rosemary, rosewood, sage, sassafras, schisandra, spikenard, spruce, star anise, tea tree, thyme, tumanu, tonka bean, vetiver, western red cedar, wintergreen, yarrow, ylang-ylang.

In some embodiments, a plant oil is a vegetable oil, an essential oil, a herbal supplement oil, or any combinations thereof.

In some embodiments, a plant is coconut oil, corn oil, cottonseed oil, olive oil, palm oil, peanut oil, rapeseed oil, canola oil, safflower oil, sesame oil, soybean oil, sunflower oil, almond oil, beech nut oil, brazil nut oil, cashew oil, hazelnut oil, macadamia oil, mongongo nut oil, pecan oil, pine nut oil, pistachio oil, walnut oil, grapefruit seed oil, lemon oil, orange oil, bitter gourd oil, buffalo gourd oil, butternut squash seed oil, pumpkin seed oil, watermelon seed oil, açai oil, black seed oil, blackcurrant seed oil, borage seed oil, flaxseed oil, amaranth oil, apricot oil, apple seed oil, argan oil, avocado oil, babassu oil, ben oil, borneo tallow nut oil, carob pod oil (algaroba oil), cocoa butter sometimes known as theobroma oil, cocklebur oil, sunflower oil, cohune oil, coriander seed oil, date seed oil, dika oil, false flax oil, grape seed oil, hemp oil, kapok seed oil, kenaf seed oil, cottonseed oil, lallemantia oil, mafura oil, marula oil, meadowfoam seed oil, mustard oil, niger seed oil, nutmeg oil, okra seed oil, perilla seed oil, persimmon seed oil, pequi oil, pili nut oil, pomegranate seed oil, poppy seed oil, pracaxi oil, prune kernel oil, quinoa oil, ramtil oil, rice bran oil, royle oil, sacha inchi oil, sapote oil, seje oil, shea oil, taramira oil, tea seed oil, tigernut oil (or nut-sedge oil), tobacco seed oil, tomato seed oil, wheat germ oil, agar oil, ajwain oil, angelica root oil, anise oil, asafoetida oil, basil oil, bay oil, bergamot oil, black pepper oil, buchu oil, birch oil, camphor oil, cannabis flower essential oil, calamodin oil, calamansi essential oil, caraway oil, cardamom seed oil, carrot seed oil, cedar oil (or cedarwood oil), chamomile oil, calamus oil, cinnamon oil, citron oil, citronella oil, clary sage oil, coconut oil, coffee oil, coriander oil, costmary oil (bible leaf oil), costus root oil, cranberry seed oil, cubeb oil, cumin oil, cypress oil, cypriol oil, curry leaf oil, davana oil, elecampane oil, elemi oil, eucalyptus oil, fennel seed oil, fenugreek oil, fir oil, frankincense oil, galangal oil, galbanum oil, geranium oil, ginger oil, goldenrod oil, helichrysum oil, hickory nut oil, horseradish oil, jasmine oil, juniper berry oil, lavender oil, melaleuca see tea tree oil, melissa oil, mint oil, moringa oil, mugwort oil, myrrh oil, myrtle neem oil or neem tree oil, oregano oil, orris oil, parsley oil, patchouli oil, perilla essential oil, pennyroyal oil, peppermint oil, pine oil, rose oil, rosehip oil, rosemary oil, rosewood oil, sage oil, sassafras oil, savory oil, schisandra oil, spearmint oil, spruce oil, star anise oil, tarragon oil, tea tree oil, thyme oil, vetiver oil (khus oil), yarrow oil or any combinations thereof.

In some embodiments, an animal oil is bone oil, cod liver oil, fish oil, goose grease, halibut-liver oil, lard oil, menhaden oil, neat's-foot oil, oleo oil, salmon oil, sardine oil, shark oil, wool oil or tallow oil.

In some embodiments, a petrochemical derived oil is mineral oil, silicone oil, petroleum, and mixtures of $C_{9-20}$ alkanes.

In some embodiments, the oil is a vitamin oil. Examples of vitamin oils include vitamin A oil, vitamin D oil, vitamin E oil, and vitamin K oil. Additional examples include oils containing retinol, retinal, carotenoid, carotene, cholecalciferol, ergocalciferol, tocopherol, tocotrienol, phylloquinone, and menaquinone.

In some embodiments, an oil is a glyceride or contains a glyceride. Examples of glycerides that can act as oils or can in oils include glycerides derived from at least one molecule of propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, crotonic acid, myristoleic acid, palmitoleic acid, sapienic acid, oleic acid, elaidic acid, vaccenic acid, erucic acid, nervonic acid, linoleic acid, eicosadienoic acid, docosadienoic acid, linolenic acid, pinolenic acid, eleostearic acid, β-eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, docosahexaenoic acid, herring acid, stearidonic acid, eicosapentaenoic acid, docosatetraenoic acid, paullinic acid, palmitoleic acid, gondoic acid, and erucic acid.

In some embodiments, an oil is a fatty acid. Examples of fatty acids that can act as oils include propanoic acid, butanoic acid, pentanoic acid, hexanoic acid, heptanoic acid, octanoic acid, nonanoic acid, decanoic acid, undecanoic acid, and dodecanoic acid. In some embodiments, the fatty acid is a C8-C16 fatty acid. In some embodiments, the fatty acid is a C12-C26 fatty acid.

In some embodiments, an oil is a phospholipid, sphingolipid, glycolipid, cholesterol, or saccharolipids.

"Preservative free multi-use applicator" refers to an applicator that can provide multiple single doses of a non-preserved formulation.

"Prevent", "preventing" or "prevention" can refer to stopping any disease, condition or symptoms or reducing symptoms in a clinically significant manner, particularly as compared to patients receiving no treatment at all.

"Prostanoids" are a subclass of eicosanoids such as prostaglandins, prostacyclin, thromboxanes and prostamides.

"Treatment", "treat" or "treating" refers to curing any disease or condition or reducing or alleviating the symptoms of the disease or condition.

Hair Growth

Prostanoids and prostamides have proven useful for increasing hair growth. In addition to restoring eyelashes and eyebrows in persons on chemotherapy, prostanoids have gained popularity and commercial success for eyelash growth. The effect of latanoprost, bimatoprost, travoprost and pharmacologically related entities on eyelashes was originally discovered during clinical trials on glaucoma patients. U.S. Pat. No. 6,626,105 teaches that prostanoids and their derivatives provide useful compounds for promoting eyelash growth. It was further reported that bimatoprost produces eyelash growth in humans. A number of reports were issued and patents filed thereafter on the prostanoids and eyelash and other hair growth, for example, U.S. Pat. No. 8,227,514. For bimatoprost specifically, the mechanism of action for increased eyelash growth has been proven to involve increased entry into anagen and extension of the anagen growth phase (Br J Dermatol. 2010 June; 162(6): 1186-97; Characterization of an in vivo model for the study of eyelash biology and trichomegaly: mouse eyelash morphology, development, growth cycle, and anagen prolongation by bimatoprost. Tauchi M, Fuchs T A, Kellenberger A J, Woodward D F, Paus R, Liitjen-Drecoll E). A similar mechanism of action has been reported for isolated human scalp hair follicles (FASEB J. 2013 February; 27(2):557-67). The prostamide-related glaucoma therapy, bimatoprost, offers one approach for treating scalp alopecias. Khidhir K G, Woodward D F, Farjo N P, Farjo B K, Tang E S, Wang J W, Picksley S M, Randall V A).

Typically, the prostanoids are formulated in aqueous solutions, dripped onto a brush, and then brushed onto the base of the eyelashes. This is the case for the FDA approved eyelash growth product Latisse®. However, aqueous solutions accelerate chemical instability of the eicosanoids and their prodrugs. For example, the prostanoid FP receptor agonist prodrug latanoprost, as the active product ingredient in Xalatan®, undergoes facile hydrolysis in aqueous solution and is stored refrigerated to retard such facile de-esterification. Eyelash growth products are typically formulated similar to eye drop products, in aqueous solution and containing a preservative such as shown in US 20080275118, EP 2498783, WO 2012038469, WO 2014158373, and US 20150025097. The use of a non-aqueous formulation such as those described above prevents de-esterification of the ester moiety of prostanoid prodrugs. These prodrugs may be alkyl esters (Stjernschantz et al., 1992; U.S. Pat. Nos. 5,510,383, 8,865,766) or phosphate esters (WO 2014070784). Prostanoids with a cyclopentenone ring in the structure are also prone to dehydration and elimination of the $H_2O$ moiety from the ring, and this process may be accelerated in aqueous formulations. Moreover, the brushes supplied in kit form are disposable and are for single use of one eye only (Latisse®, see product use instructions). There is unavoidable waste in this procedure and is costly in terms of raw materials. For example, bimatoprost costs about one million two hundred thousand U.S. dollars per kilogram and is therefore very expensive to use in a hair-growth formulation. Further, the brush must be soaked in aqueous formulation and much of this cannot be transposed onto the eyelid and is inextricably held within the brush. Moreover, the aqueous solutions sometimes drop off the brush.

Preservatives are often regarded as an unwanted necessity, preserving the formulation but with deleterious effects on the eye. One common solution to the problem of preservation is to dispense the product in a unit dose form. However, unit dose packaging is significantly more expensive than multi-dose packaging, adding to the cost of the final product. For example, with the product Latisse®, a preserved solution is supplied with single-use, disposable brush applicators. This greatly adds to the cost of the final product. When eicosanoids are formulated in a non-aqueous formulation, the need for a preservative is removed. This permits the use of multiple dose delivery from a single applicator, which is easier for carrying and travel around.

Dry Eye Disease

Dry eye has many root causes and these diverse etiological origins translates into an estimated 5-35% of affected persons worldwide. The full impact of "dry eye" may not be felt for a couple of decades until the contributions of environmental and, increasingly, situational factors and the exacerbations associated with an aging population are made manifest. Environmental factors include gaseous pollution, dust, dry air, wind, and heat. Situational factors are largely related to TV, computer, and cellphone screens. The drastically reduced blinking rate caused by watching at computer screens results in "dry eye" due to a lack of irrigation of the ocular surface. Dry eye disease is a separate entity, although the symptomology may be similar. Dry eye disease is a diagnosed inflammatory/autoimmune disease that affects the lacrimal gland and reduces tear secretion. Dry eye of all origins, if allowed to continue without remedial intervention, could eventually worsen to the point where effects on the cornea compromise daily life; driving, working (M Meadows, *FDA Consumer Magazine*, May-June, 2005; Nichols K K, et al. *Invest Ophthalmol Vis Sci* 57; 2975-2982, 2016).

Tears moisten and lubricate the cornea and are composed of aqueous, mucus, and highly complex lipid components (Butovich I A et al. *Biochim Biophys Acta* 1861; 538-553, 2016; Chen J et al. *Invest Ophthalmol Vis Sci* 58; 2266-2274, 2017). The aqueous film provided by the tears is of modest benefit in itself, the watery tears associated with irritation or emotion give little or no relief from dry eye. Lack of lubrication is considered important in the development of "dry eye" (Knop E et al. *Invest Ophthalmol Vis Sci* 52; 1938-1978, 2011). The Meibomian gland secretion, meibum, is composed of numerous lipid species rendering it difficult to directly replace.

Apart from immunologically-based dry eye disease, dry eye is treated with lubricating aqueous solutions, purported to be artificial tears. The lubrication ingredient is typically man-made and not a naturally occurring substance. These lubricants include hydroxypropylmethyl cellulose, carboxymethyl cellulose, polyvinyl alcohol, glycerin, hyaluronic acid, polysorbate, propylene glycol, and polyethylene glycol. Tear replacements include preservatives. The safety profiles of the preservatives vary but damage to the corneal epithelium occurs at all high doses and it is recommended that administration of such artificial tears should be limited to 4 to 6 times a day (Moshirfar M et al. *Clin Ophthalmol* 8: 1419-1433, 2014).

Compositions and Methods of Use

Hair Growth

Some embodiments of the present invention include:
A) A non-aqueous, non-preserved formulation for use in treating one selected from the group consisting of the eyelashes, hair loss of the eyebrows or hair loss of the scalp, comprised of bimatoprost, ethanol, and at least one plant oil, such as jojoba oil, castor oil, avocado oil, olive oil, sweet almond oil and optionally at least one essential oil.
B) The non-aqueous, non-preserved formulation of embodiment A wherein the formulation is for treatment of hypotrichosis of the eyelashes and the bimatoprost is present in a concentration of 0.01%-0.03% w/v.
C) The non-aqueous, non-preserved formulation of embodiment B wherein the formulation is applied to at least one eyelid margin for treatment of hypotrichosis of the eyelashes.
D) The non-aqueous, non-preserved formulation of embodiment C wherein the formulation is applied to the upper eyelid margin.
E) The non-aqueous, non-preserved formulation of embodiment D wherein the formulation is applied once a day.
F) The non-aqueous, non-preserved formulation of embodiment E wherein the formulation comprises ethanol, castor oil and jojoba oil.
G) The non-aqueous, non-preserved formulation of embodiment F wherein the formulation further comprises one oil selected from the group consisting of avocado oil, olive oil and sweet almond oil.
H) The non-aqueous, non-preserved formulation of embodiment G wherein the formulation further comprises one oil selected from the group consisting of castor oil, avocado oil, jojoba oil, olive oil, sweet almond oil, vitamin E.
I) The non-aqueous, non-preserved formulation of embodiment A comprising bimatoprost, absolute ethanol, castor oil and jojoba oil.
J) The non-aqueous, non-preserved formulation of embodiment I comprising about 0.03% w/v bimatoprost, about 1% v/v ethanol, about 3% v/v castor oil and about 96% v/v jojoba oil.
K) The formulation of embodiment B wherein the formulation is applied to the eyelid margins by a multi-use applicator.
L) The formulation of embodiment B comprising 0.02%-0.03% w/v bimatoprost, about 1% v/v ethanol, about 3% v/v castor oil, and about 70-96% v/v jojoba oil.
M) The formulation of embodiment L comprising 0.02% w/v bimatoprost.
N) The formulation of embodiment M wherein the formulation applied once a day to the eyelid margins avoids ocular side effects to a greater degree as compared to a 0.03% w/v bimatoprost solution applied once a day to the eyelid margins.
O) The formulation of embodiment M wherein application of the formulation results in more bimatoprost delivered to the eyelid margin by a single application than a 0.03% w/v solution of bimatoprost.
P) The formulation of embodiment M wherein the formulation results in equal or greater eyelash growth than a 0.03% w/v solution of bimatoprost.
Q) The formulation of embodiment B wherein the once daily application of the formulation to a patient results in eyelashes that are longer, denser and darker than a patient not applying the formulation.
R) The formulation of embodiment B wherein the formulation applied to the upper eyelid once a day results in longer eyelashes within 60 days.
S) The formulation of embodiment A wherein the formulation is applied to one selected from the group consisting of upper eyelid margin, eyebrows and the scalp.
T) The formulation of embodiment S wherein the formulation results in increased hair growth of at least one selected from the group consisting of eyelashes, eyebrows and scalp hair.
U) A formulation for eyelash or eyebrow growth selected from any formulation of Tables I-IV.
V) A formulation for scalp hair growth or eyebrow hair growth selected from any formulations of Tables I-IV.
W) The formulation of embodiment V wherein the formulation is applied to the eyebrows or scalp once a day.
X) The formulation of embodiment V wherein the formulation is applied to the eyebrows or scalp twice a day.
Y) The formulation of embodiment W wherein once daily application causes increased scalp hair or eyebrow growth.
Z) Use of one selected from the group consisting of bimatoprost, latanoprost, tafluprost and travoprost for increasing one selected from the group consisting of eyelash growth, eyebrow growth or scalp hair growth.
AA) A prostanoid and a natural oil to aid activity, improve hair appearance, provide hair follicle nourishment, improve hair shaft curl, or aid solubility selected from the group consisting of angelica root, balsam of Peru, basil, camphor, cannabis flower, cardamom, carrot seed, cedarwood, chamomile, calamus, cinnamon, cistus, citron, citronella, clary sage, clove, coriander, costus root, cranberry seed, cumin, cypress, davana, elecampane, eucalyptus, fennel seedfrankincense, galangal, galbanum, geranium, goldenrod, grapefruit seed, henna, helichrysum, hickory nut, Idaho tansy, jasmine, juniper berry, *Laurus nobilis*, lavender, ledum, lemongrass, mandarin, menthe arvensis, moringa, mountain savory, mugwort, myrrh, neroli, nutmeg, parsley, patchouli, perilla, pennyroyal, petitgrain, red cedar, rose, rosehip, rosemary, rosewood, sage, sassafras, schisandra, spikenard, spruce, star anise, tea tree, thyme, tumanu, tonka bean, vetiver, western red cedar, wintergreen, yarrow, ylang-ylang. Triglycerides extracted from plants and their seeds are also contemplated as useful as a solvent, medicinal, and/or cosmetic properties that may be selected from the following oils: almond, argan, avocado, beech nut, blackcurrant seed, brazil nut, butternut squash seed, camellia (tea seed), cape chestnut, cashew nut, castor, cocoa butter, coconut, corn, cottonseed, flaxseed, grape seed, hazelnut, hemp seed, jojoba, kapok seed, kenaf seed, okra seed, olive, palm, peanut, pomegranate seed, poppyseed, soybean, sunflower seed and mixtures thereof.
BB) A composition for hair growth comprising an oil formulation and an eicosanoid.
CC) The composition of embodiment BB wherein the oil formulation is non-aqueous.

In order to improve eyelash/eyebrow hair growth products, health and appearance enhancement and nutrients may be added to the formulations. Uniquely for the eyelashes, ingredients to permit curling (WO 2000074519, WO 2007078861, WO 20090136439 all of which are incorporated by reference), and thereby enhancing appearance and preventing impingement on the eyeball and ingrowth, would be useful.

The invention pertains to non-aqueous formulations of eicosanoids which allow the formulation to be preservative-free and assists in the chemical stabilization of the active product ingredient. Non-aqueous and non-preserved formulations containing an eicosanoid, such as a prostanoid, and in particular bimatoprost, tafluprost, or travoprost, and nutrient/health care ingredients have been devised as described herein. These ingredients are essential oils and plant oils. As preference, a cylindrical device fitted with a felt/fiber tip is a method for eyelid margin delivery. This delivery method results in economic advantages, such as less waste since the product is applied only to the discrete area requiring hypertrichosis and minimal unintentional retention by the applicator compared to brushes. Dosing may be once every other day, once a day, twice a day or three times a day. The formulations may be applied to either the upper or lower eyelid margin, eyebrows or the scalp.

The eyelash growth formulation may be delivered precisely to the eyelid margin by the use of specialized devices designed for the purpose. For example, specialized devices have been suggested for this purpose of precision delivery to the required site (US 20070160562). Brush (WO2010065487) and roller devices (US 20070160562) have been contemplated at the contact end of the device. The "tip" could also be in the form of a rotating cylinder or a felt/fiber tip. To assist in accurately delivering a therapeutic amount of the desired eicosanoid, a cylindrical reservoir may be employed. The device may incorporate positive displacement of the formulation by a plunger or by a ratchet that may be turned to deliver the formulation. The cylinder reservoir may be graduated to assist in quantifying drug delivery.

Direct delivery of the natural oil based drug formulation to the required site of action, namely the eyelid margin, has certain advantages. The spread of drug to areas where it can be of little or no hypertrichotic benefit (for example on the upper eyelids or eyelash hair shafts per se) is minimized. Direct delivery to the eyelid margins also minimizes the possibility of drug accessing the globe, where it would produce an unwanted decrease in intraocular pressure. The use of a natural oil based vehicle with a felt/fiber tip positive displacement device reduces waste. There is a continuous flow/retention of formulation into the tip that is easily replenished and which is not prone to evaporation. This contrasts with aqueous formulations which are added to a brush, or the brush is dipped into the aqueous formulation. In such cases, most of the material remains unused in the brush and is lost by disposal of the brush, and evaporation if the brush is retained and used again contrary to the manufacturer's instructions. In some cases, solution drip from the brush results in waste of material. These brush application methods possess economic disadvantages that are avoided by the inventions described herein.

Some eyelash formulations are listed below:

TABLE I

| Formulation No. | 1 | 2 | 3 | 4 | 5 | 6 |
|---|---|---|---|---|---|---|
| Bimatoprost (w/v) | 0.01% | 0.02% | 0.03% | 0.01% | 0.02% | 0.03% |
| Ethanol (v/v) | 1% | 1% | 1% | 1% | 1% | 1% |
| Castor Oil (v/v) | 3% | 3% | 3% | 3% | 3% | 3% |
| Jojoba Oil (v/v) | 96% | 96% | 96% | 94-95.5% | 94-95.5% | 94-95.5% |
| Essential Oils (v/v) | 0% | 0% | 0% | 0.5-2% | 0.5-2% | 0.5-2% |

The invention includes concentrations of active agent including 3.0% w/v to 0.001% w/v and including concentrations such as 3.0%, 2.0%, 1.0% w/v, 0.9% w/v, 0.8% w/v, 0.7% w/v, 0.6% w/v, 0.5% w/v, 0.4% w/v, 0.3% w/v, 0.2% w/v, 0.1% w/v, 0.09% 0.08% w/v, 0.07% w/v, 0.06% w/v, 0.05% w/v, 0.04% w/v, 0.03% w/v, 0.02% w/v, 0.01% w/v, 0.009% w/v, 0.008% w/v, 0.007% w/v, 0.006% w/v, 0.005% w/v, 0.004% w/v, 0.003% w/v, 0.002% w/v, 0.001% w/v, 0.009% w/v, 0.008% w/v, 0.007% w/v, 0.006% w/v, 0.005% w/v, 0.004% w/v, 0.003% w/v, 0.002% w/v, and 0.001% w/v bimatoprost, travoprost, tafluprost or latanoprost. Other oils include lavendar essential oil, cedarwood essential oil, thyme essential oil, clary sage essential oil and rosemary essential oil, avocado oil, sweet almond oil and jojoba.

Additional eyelash formulations are below:

TABLE II

| Formulation No. | 7 | 8 | 9 | 10 | 11 | 12 | 13 | 14 | 15 | 16 | 17 | 18 |
|---|---|---|---|---|---|---|---|---|---|---|---|---|
| Bimatoprost (wt/v) % | 0.01 | 0.01 | 0.01 | 0.01 | 0.02 | 0.02 | 0.02 | 0.02 | 0.03 | 0.03 | 0.03 | 0.03 |
| Ethanol (v/v) % | 1 | 1 | 1 | 1 | 1 | 1 | 1 | 1 | 1 | 1 | 1 | 1 |
| Castor Oil (v/v) % | 3 | 3 | 3 | 3 | 3 | 3 | 3 | 3 | 3 | 3 | 3 | 3 |
| Jojoba oil (v/v) % | 95.6 | 71.6 | 71.6 | 71.6 | 95.6 | 71.6 | 71.6 | 71.6 | 95.6 | 71.6 | 71.6 | 71.6 |
| Olive oil (v/v) % | | 24 | | 12 | | 24 | | 12 | | 24 | | 12 |
| Sweet almond oil (v/v) % | | | 24 | 12 | | | 24 | 12 | | | 24 | 12 |
| Vitamin E (v/v) % | 0.4 | 0.4 | 0.4 | 0.4 | 0.4 | 0.4 | 0.4 | 0.4 | 0.4 | 0.4 | 0.4 | 0.4 |

TABLE III

| Formulation No. | 19 | 20 | 21 | 22 | 23 | 24 | 25 |
|---|---|---|---|---|---|---|---|
| Bimatoprost (wt/v) % | 0.1 | 0.1 | 0.1 | 0.1 | 0.1 | 0.1 | 0.1 |
| Ethanol (v/v) % | 3 | 3 | 3 | 3 | 3 | 3 | 3 |
| Castor Oil (v/v) % | 3 | 3 | 3 | 3 | 3 | 3 | 3 |
| Jojoba oil (v/v) % | 68.5 | 68.5 | 68.5 | 68.5 | 68.5 | 68.5 | 68.5 |
| Avocado oil (v/v) % | 24 | | | 12 | 12 | | 8 |
| Olive oil (v/v) % | | 24 | | 12 | | 12 | 8 |
| Sweet almond oil (v/v) % | | | 24 | | 12 | 12 | 8 |
| Rosemary Oil (v/v) % | 0.5 | 0.5 | 0.5 | 0.5 | 0.5 | 0.5 | 0.5 |
| Tea tree oil (v/v) % | 0.5 | 0.5 | 0.5 | 0.5 | 0.5 | 0.5 | 0.5 |
| Vitamin E (v/v) % | 0.5 | 0.5 | 0.5 | 0.5 | 0.5 | 0.5 | 0.5 |

TABLE IV

| Formulation No. | 26 | 27 | 28 | 29 | 30 | 31 | 32 |
|---|---|---|---|---|---|---|---|
| Bimatoprost (wt/v) % | 0.3 | 0.3 | 0.3 | 0.3 | 0.3 | 0.3 | 0.3 |
| Ethanol (v/v) % | 7 | 7 | 7 | 7 | 7 | 7 | 7 |
| Castor Oil (v/v) % | 3 | 3 | 3 | 3 | 3 | 3 | 3 |
| Jojoba oil (v/v) % | 64.5 | 64.5 | 64.5 | 64.5 | 64.5 | 64.5 | 64.5 |
| Avocado oil (v/v) % | 24 | | | 12 | 12 | | 8 |
| Olive oil (v/v) % | | 24 | | 12 | | 12 | 8 |
| Sweet almond oil (v/v) % | | | 24 | | 12 | 12 | 8 |
| Rosemary Oil (v/v) % | 0.5 | 0.5 | 0.5 | 0.5 | 0.5 | 0.5 | 0.5 |
| Tea tree oil (v/v) % | 0.5 | 0.5 | 0.5 | 0.5 | 0.5 | 0.5 | 0.5 |
| Vitamin E (v/v) % | 0.5 | 0.5 | 0.5 | 0.5 | 0.5 | 0.5 | 0.5 |

Eyebrow growth formulations or scalp hair growth formulations may be the same as those listed in Tables I-IV.

Dry Eye

It was discovered that the bimatoprost formulation provided significant relief from dry eye symptoms. To better understand the origin of this beneficial effect on dry eye symptomology, a composition was formulated without bimatoprost or ethanol and evaluated in human volunteers with dry eye symptomology. Significant improvement or relief of dry eye was experienced.

TABLE V

| Formulation No. | 33 |
|---|---|
| Bimatoprost (w/v) | 0.03% |
| Ethanol (v/v) | 1% |
| Castor Oil (v/v) | 3% |
| Jojoba Oil (v/v) | 96% |
| Essential Oils (v/v) | 0% |

TABLE VI

| Formulation No. | 34 |
| --- | --- |
| Castor Oil (v/v) | 3% |
| Jojoba Oil (v/v) | 71.6% |
| Sweet almond oil (v/v) | 24% |
| Vitamin E (v/v) | 0.4% |

Dry eye relief formulations may be the same as those listed in Tables I-VI

Additional embodiments of the present invention include:

1. In one embodiment is a formulation for the stimulation of hair growth wherein the formulation is comprised of:
   at least one eicosanoid;
   at least one oil; and
   at least one alcohol; wherein
   the formulation is substantially free of water; and
   the formulation is substantially free of preservatives.

2. The formulation of embodiment 1, wherein the concentration of eicosanoid is from about 0.001% to about 5.0%.

3. The formulation of embodiment 1, wherein the concentration of eicosanoid is from about 0.01% to about 3.0%.

4. The formulation of embodiment 1, wherein the concentration of eicosanoid is from about 0.1% to about 0.3%.

5. The formulation of embodiment 1, wherein the concentration of eicosanoid is from about 0.01% to about 0.05%.

6. The formulation of any one of embodiments 1-5, wherein the eicosanoid is a prostanoid, leukotriene, lipoxin, resolvin, or eoxin.

7. The formulation of embodiment 6, wherein the eicosanoid is a prostanoid.

8. The formulation of embodiment 7, wherein the eicosanoid is a prostanoid selected from prostaglandin $F_{2\alpha}$, dinoprost, latanoprost, bimatoprost, travoprost, carboprost, and tafluprost.

9. The formulation of embodiment 8, wherein the prostanoid is bimatoprost.

10. The formulation of embodiment 8, wherein the prostanoid is prostaglandin $F_{2\alpha}$.

11. The formulation of embodiment 8, wherein the prostanoid is dinoprost.

12. The formulation of embodiment 8, wherein the prostanoid is latanoprost.

13. The formulation of embodiment 8, wherein the prostanoid is travoprost.

14. The formulation of embodiment 8, wherein the prostanoid is carboprost.

15. The formulation of embodiment 8, wherein the prostanoid is tafluprost.

16. In one embodiment is a formulation for use in treating a condition selected from the group consisting of hypotrichosis of the eyelashes, hair loss of the eyebrows, hair loss of the scalp, and hypotrichosis associated with chemotherapy treatment regimens, wherein the formulation is comprised of:
   bimatoprost;
   at least one oil; and
   at least one alcohol; wherein
   the formulation is substantially free of water; and
   the formulation is substantially free of preservatives.

17. The formulation of any one of embodiments 1-16, wherein the concentration of oil is from about 0.1% to about 99.0%.

18. The formulation of any one of embodiments 1-16, wherein the concentration of oil is from about 50.0% to about 99.0%.

19. The formulation of any one of embodiments 1-16, wherein the concentration of oil is from about 40.0% to about 50.0%.

20. The formulation of any one of embodiments 1-16, wherein the concentration of oil is from about 50.1% to about 60.0%.

21. The formulation of any one of embodiments 1-16, wherein the concentration of oil is from about 60.1% to about 70.0%.

22. The formulation of any one of embodiments 1-16, wherein the concentration of oil is from about 70.1% to about 80.0%.

23. The formulation of any one of embodiments 1-16, wherein the concentration of oil is from about 80.1% to about 90.0%.

24. The formulation of any one of embodiments 1-16, wherein the concentration of oil is from about 90.1% to about 99.0%.

25. The formulation of any one of embodiments 1-16, wherein the concentration of oil is from about 40.0% to about 55.0%.

26. The formulation of any one of embodiments 1-16, wherein the concentration of oil is from about 55.1% to about 70.0%.

27. The formulation of any one of embodiments 1-16, wherein the concentration of oil is from about 70.1% to about 85.0%.

28. The formulation of any one of embodiments 1-16, wherein the concentration of oil is from about 85.1% to about 99.0%.

29. The formulation of any one of embodiments 1-16, wherein the concentration of oil is about 93%.

30. The formulation of any one of embodiments 1-16, wherein the concentration of oil is about 95%.

31. The formulation of any one of embodiments 1-16, wherein the concentration of oil is about 97%.

32. The formulation of any one of embodiments 1-16, wherein the concentration of oil is about 99%.

33. The formulation of any one of embodiments 1-32, wherein the concentration of alcohol is from about 0.1% to about 50.0%.

34. The formulation of any one of embodiments 1-32, wherein the concentration of alcohol is from about 0.1% to about 20.0%.

35. The formulation of any one of embodiments 1-32, wherein the concentration of alcohol is from about 1.0% to about 15.0%.

36. The formulation of any one of embodiments 1-32, wherein the concentration of alcohol is from about 1.0% to about 10.0%.

37. The formulation of any one of embodiments 1-32, wherein the concentration of alcohol is from about 3.0% to about 10.0%.

38. The formulation of any one of embodiments 1-32, wherein the concentration of alcohol is from about 1.0% to about 5.0%.

39. The formulation of any one of embodiments 1-32, wherein the concentration of alcohol is from about 3.0% to about 8.0%.

40. The formulation of any one of embodiments 1-32, wherein the concentration of alcohol is from about 3.0% to about 5.0%.

41. The formulation of any one of embodiments 1-40, wherein substantially free of water is defined as less than 5.0%.

42. The formulation of any one of embodiments 1-40, wherein substantially free of water is defined as less than 2.0%.

43. The formulation of any one of embodiments 1-40, wherein substantially free of water is defined as less than 1.0%.

44. The formulation of any one of embodiments 1-40, wherein substantially free of water is defined as less than 0.5%.

45. The formulation of any one of embodiments 1-40, wherein substantially free of water is defined as less than 0.1%.

46. The formulation of any one of embodiments 1-40, wherein substantially free of water is defined as less than 0.05%.

47. The formulation of any one of embodiments 1-40, wherein substantially free of water is defined as less than 0.01%.

48. The formulation of any one of embodiments 1-40, wherein substantially free of water is defined as less than 0.005%.

49. The formulation of any one of embodiments 1-40, wherein substantially free of water is defined as less than 0.001%.

50. The formulation of any one of embodiments 1-49, wherein substantially free of preservative is defined as less than 5.0%.

51. The formulation of any one of embodiments 1-49, wherein substantially free of preservative is defined as less than 2.0%.

52. The formulation of any one of embodiments 1-49, wherein substantially free of preservative is defined as less than 1.0%.

53. The formulation of any one of embodiments 1-49, wherein substantially free of preservative is defined as less than 0.5%.

54. The formulation of any one of embodiments 1-49, wherein substantially free of preservative is defined as less than 0.1%.

55. The formulation of any one of embodiments 1-49, wherein substantially free of preservative is defined as less than 0.05%.

56. The formulation of any one of embodiments 1-49, wherein substantially free of preservative is defined as less than 0.01%.

57. The formulation of any one of embodiments 1-49, wherein substantially free of preservative is defined as less than 0.005%.

58. The formulation of any one of embodiments 1-49, wherein substantially free of preservative is defined as less than 0.001%.

59. The formulation of embodiment 16, wherein the concentration of bimatoprost is from about 0.001% to about 5.0%.

60. The formulation of embodiment 16, wherein the concentration of bimatoprost is from about 0.01% to about 3.0%.

61. The formulation of embodiment 16, wherein the concentration of bimatoprost is from about 0.01% to about 1.0%.

62. The formulation of embodiment 16, wherein the concentration of bimatoprost is from about 0.01% to about 0.5%.

63. The formulation of embodiment 16, wherein the concentration of bimatoprost is from about 0.02% to about 0.4%.

64. The formulation of embodiment 16, wherein the concentration of bimatoprost is from about 0.03% to about 0.3%.

65. The formulation of embodiment 16, wherein the concentration of bimatoprost is from about 0.1% to about 0.3%.

66. The formulation of embodiment 16, wherein the concentration of bimatoprost is from about 0.1% to about 0.2% 67. The formulation of embodiment 16, wherein the concentration of bimatoprost is from about 0.005% to about 0.05%.

68. The formulation of embodiment 16, wherein the concentration of bimatoprost is about 0.01%.

69. The formulation of embodiment 16, wherein the concentration of bimatoprost is about 0.02%.

70. The formulation of embodiment 16, wherein the concentration of bimatoprost is about 0.03%.

71. The formulation of embodiment 16, wherein the concentration of bimatoprost is about 0.04%.

72. The formulation of embodiment 16, wherein the concentration of bimatoprost is about 0.05%.

73. The formulation of any one of embodiments 1-72 for use in treating a condition selected from the group consisting of hypotrichosis of the eyelashes, hair loss of the eyebrows, hair loss of the scalp, and hypotrichosis associated with chemotherapy treatment regimens.

74. The formulation of any one of embodiments 1-73, for use in treating hypotrichosis of the eyelashes.

75. The formulation of any one of embodiments 1-73, for use in treating hair loss of the eyebrows.

76. The formulation of any one of embodiments 1-73, for use in treating hair loss of the scalp.

77. The formulation of any one of embodiments 1-73, for use in treating hypotrichosis associated with chemotherapy treatment regimens.

78. The formulation of any one of embodiments 1-77, wherein at least one alcohol is a $C_1$-$C_{20}$ alcohol.

79. The formulation of embodiment 78, wherein the alcohol is at least one $C_1$-$C_{10}$ alcohol.

80. The formulation of embodiment 79, wherein the alcohol is at least one $C_1$-$C_6$ alcohol.

81. The formulation of embodiment 80, wherein the alcohol is at least one $C_1$-$C_3$ alcohol.

82. The formulation of embodiment 79, wherein at least one alcohol is selected form the group of methanol, ethanol, 1-propanol, 1-butanol, 1-pentanol, propan-2-ol, 2-methylpropan-1-ol, butan-2-ol, 2-methylpropan-2-ol, 3-methylbutan-2-ol, 3-methylbutan-1-ol, 2-methylbutan-1-ol and 2-methylbutan-2-ol, pentan-3-ol, 2-methylpentan-2-ol, 2-methylpentan-3-ol, 4-methylpentan-2-ol, 4-methylpentan-1-ol, 2-methylpentan-1-ol, 3-methylpentan-1-ol, 3-methylpentan-2-ol, 3-methylpentan-3-ol, hexan-2-ol, hexan-3-ol, 2-methylhexan-1-ol, 2-methylhexan-2-ol, 2-methylhexan-3-ol, 5-methylhexan-3-ol, 5-methylhexan-2-ol, 5-methylhexan-1-ol, 3-methylhexan-1-ol, 3-methylhexan-2-ol, 3-methylhexan-3-ol, 4-methylhexan-3-ol, 4-methylhexan-2-ol, and 4-methylhexan-1-ol.

83. The formulation of embodiment 82, wherein at least one alcohol is selected from the group of ethanol, 1-propanol, 2-propanol and 1-butanol.

84. The formulation of embodiment 83, wherein the alcohol is ethanol.

85. The formulation of embodiment 83, wherein the alcohol is 2-propanol.

86. The formulation of any one of embodiments 1-85, wherein at least one oil is a plant oil.

87. The formulation of any one of embodiments 1-85, wherein at least one oil is an animal oil.

88. The formulation of any one of embodiments 1-85, wherein at least one oil is a petroleum based oil.

89. The formulation of any one of embodiments 1-85, wherein at least one oil is not a plant or animal based oil.

90. The formulation of any one of embodiments 1-85, wherein at least one oil is selected from the group consisting of castor oil, avocado oil, jojoba oil, olive oil, rosemary oil, tea tree oil, sweet almond oil, and vitamin E.

91. The formulation of any one of embodiments 1-85, wherein at least one oil is selected from the group consisting of lavendar essential oil, cedarwood essential oil, thyme essential oil, clary sage essential oil, rosemary essential oil, polygonum multiflorum, castor oil, jojoba oil, avocado oil, olive oil, sweet almond oil, vitamin E.

92. The formulation of any one of embodiments 1-85, wherein at least two or more oils are selected from the group consisting of avocado oil, olive oil, sweet almond oil, castor oil, rosemary oil, tea tree oil, jojoba oil, and vitamin E.

93. The formulation of any one of embodiments 1-92, wherein the formulation is applied once every 7 days.

94. The formulation of any one of embodiments 1-92, wherein the formulation is applied once every 2 days.

95. The formulation of any one of embodiments 1-92, wherein the formulation is applied once per day.

96. The formulation of any one of embodiments 1-92, wherein the formulation is applied twice per day.

97. The formulation of any one of embodiments 1-92, wherein the formulation is applied three times per day.

98. The formulation of any one of embodiments 1-97, wherein the formulation is applied to an area of skin containing at least one hair follicle.

99. The formulation of any one of embodiments 1-97, wherein the formulation is applied to an area selected from the group consisting of upper eyelid margin, eyebrows and the scalp.

100. The formulation of embodiment any one of embodiments 1-97, wherein the formulation is applied to the face, the scalp or the body.

101. The formulation of embodiment 100, wherein the formulation is applied to the face.

102. The formulation of any one of embodiments 1-101, wherein the formulation is applied to at least one eyelid margin.

103. The formulation of embodiment 102, wherein the formulation is applied to at least one upper eyelid margin.

104. The formulation of any one of embodiments 1-103, wherein the formulation elongates eyelash hairs by daily application over a period of 60 days.

105. The formulation of any one of embodiments 1-104, wherein the formulation is applied by a multi-use applicator.

106. The formulation of any one of embodiments 1-105, wherein the alcohol is ethanol and the oil is a combination of castor oil and jojoba oil.

107. The formulation of embodiment 16, wherein the formulation comprises about 0.02% w/v bimatoprost, about 1% v/v ethanol, about 3% v/v castor oil, about 71.6% v/v jojoba oil, about 24% v/v sweet almond oil, and about 0.4% v/v Vitamin E.

108. The formulation of embodiment 16, wherein the formulation comprises 0.03% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil and 0.5% v/v Vitamin E.

109. The formulation of embodiment 16, wherein the formulation comprises 0.01% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E.

110. The formulation of embodiment 16, wherein the formulation comprises 0.02%-0.03% w/v bimatoprost, about 1% v/v ethanol, about 3% v/v castor oil, and about 70-96% v/v jojoba oil.

111. The formulation of embodiment 16, wherein
the concentration of bimatoprost is 0.02%;
the formulation is delivered to at least one upper eyelid margin;
the formulation is delivered with a multi-use applicator; and
the formulation results in equal or greater eyelash growth when compared to a water-based formulation with a concentration of bimatoprost of 0.03%.

112. The formulation of embodiment 111, wherein the water-based formulation is applied with a single use applicator.

113. The formulation of embodiment 111, wherein the water-based formulation is applied with a brush contacting the eyelashes.

114. In one embodiment is a formulation for use in treating a condition selected from the group consisting of hypotrichosis of the eyelashes, hair loss of the eyebrows, hair loss of the scalp, and hypotrichosis associated with chemotherapy treatment regimens, wherein the formulation is comprised of bimatoprost and an optionally substituted $C_7$-$C_{20}$ alkanol.

115. The formulation of embodiment 114, wherein the substituted $C_7$-$C_{20}$ alkyl is substituted with one or more groups selected from: —OH, —O—R, —NH$_2$, —NHR, —NR$_2$, —C(=O)H, —C(=O)R, —C(=O)OH, —C(=O)OR, —OC(=O)R, —SH, —SR, and —S(=O)$_2$R; wherein R is unsubstituted $C_1$-$C_{10}$ alkyl.

116. The formulation of embodiment 115, wherein the substituted $C_7$-$C_{20}$ alkyl is substituted with one or more groups selected from: —OH, —O—R, —C(=O)OR, and —OC(=O)R.

117. In one embodiment is a formulation comprising bimatoprost, an oil, and an alcohol, for use in:
i) treating a condition selected from the group consisting of hypotrichosis of the
eyelashes, hair loss of the eyebrows or hair loss of the scalp;
ii) regenerating hair on the face, scalp or body;
iii) modifying at least one hair in length, base circumference, rigidity, or color;
iv) increasing the number of hairs per area of skin; or
v) converting villous hair to terminal hair.

118. In one embodiment is a formulation for use in treating a condition selected from the group consisting of hypotrichosis of the eyelashes, hair loss of the eyebrows, hair loss of the scalp, and hypotrichosis associated with chemotherapy treatment regimens, wherein the formulation consists essentially of:
bimatoprost;
at least one oil; and
at least one alcohol; wherein
the formulation is substantially free of water; and
the formulation is substantially free of preservatives.

119. The formulation of embodiment 118, wherein the concentration of oil is from about 0.1% to about 99.0%.

120. The formulation of embodiment 118, wherein the concentration of oil is from about 50.0% to about 99.0%.

121. The formulation of embodiment 118, wherein the concentration of oil is from about 40.0% to about 50.0%.

122. The formulation of embodiment 118, wherein the concentration of oil is from about 50.0% to about 60.0%.

123. The formulation of embodiment 118, wherein the concentration of oil is from about 60.0% to about 70.0%.

124. The formulation of embodiment 118, wherein the concentration of oil is from about 70.0% to about 80.0%.

125. The formulation of embodiment 118, wherein the concentration of oil is from about 80.0% to about 90.0%.

126. The formulation of embodiment 118, wherein the concentration of oil is from about 90.0% to about 99.0%.

127. The formulation of embodiment 118, wherein the concentration of oil is from about 40.0% to about 55.0%.

128. The formulation of embodiment 118, wherein the concentration of oil is from about 55.0% to about 70.0%.

129. The formulation of embodiment 118, wherein the concentration of oil is from about 70.0% to about 85.0%.

130. The formulation of embodiment 118, wherein the concentration of oil is from about 85.0% to about 99.0%.

131. The formulation of embodiment 118, wherein the concentration of oil is about 93%.

132. The formulation of embodiment 118, wherein the concentration of oil is about 95%.

133. The formulation of embodiment 118, wherein the concentration of oil is about 97%.

134. The formulation of embodiment 118, wherein the concentration of oil is about 99%.

135. The formulation of any one of embodiments 118-134, wherein the concentration of alcohol is from about 0.1% to about 50.0%.

136. The formulation of any one of embodiments 118-134, wherein the concentration of alcohol is from about 0.1% to about 20.0%.

137. The formulation of any one of embodiments 118-134, wherein the concentration of alcohol is from about 1.0% to about 15.0%.

138. The formulation of any one of embodiments 118-134, wherein the concentration of alcohol is from about 1.0% to about 10.0%.

139. The formulation of any one of embodiments 118-134, wherein the concentration of alcohol is from about 3.0% to about 10.0%.

140. The formulation of any one of embodiments 118-134, wherein the concentration of alcohol is from about 1.0% to about 5.0%.

141. The formulation of any one of embodiments 118-134, wherein the concentration of alcohol is from about 3.0% to about 8.0%.

142. The formulation of any one of embodiments 118-134, wherein the concentration of alcohol is from about 3.0% to about 5.0%.

143. The formulation of any one of embodiments 118-142, wherein substantially free is defined as less than 5.0%.

144. The formulation of any one of embodiments 118-142, wherein substantially free is defined as less than 2.0%.

145. The formulation of any one of embodiments 118-142, wherein substantially free is defined as less than 1.0%.

146. The formulation of any one of embodiments 118-142, wherein substantially free is defined as less than 0.5%.

147. The formulation of any one of embodiments 118-142, wherein substantially free is defined as less than 0.1%.

148. The formulation of any one of embodiments 118-142, wherein substantially free is defined as less than 0.05%.

149. The formulation of any one of embodiments 118-142, wherein substantially free is defined as less than 0.01%.

150. The formulation of any one of embodiments 118-142, wherein substantially free is defined as less than 0.005%.

151. The formulation of any one of embodiments 118-142, wherein substantially free is defined as less than 0.001%.

152. The formulation of any one of embodiments 118-151, wherein the concentration of bimatoprost is from about 0.001% to about 5.0%.

153. The formulation of any one of embodiments 118-151, wherein the concentration of bimatoprost is from about 0.01% to about 3.0%.

154. The formulation of any one of embodiments 118-151, wherein the concentration of bimatoprost is from about 0.01% to about 1.0%.

155. The formulation of any one of embodiments 118-151, wherein the concentration of bimatoprost is from about 0.01% to about 0.5%.

156. The formulation of any one of embodiments 118-151, wherein the concentration of bimatoprost is from about 0.02% to about 0.4%.

157. The formulation of any one of embodiments 118-151, wherein the concentration of bimatoprost is from about 0.03% to about 0.3%.

158. The formulation of any one of embodiments 118-151, wherein the concentration of bimatoprost is from about 0.1% to about 0.3%.

159. The formulation of any one of embodiments 118-151, wherein the concentration of bimatoprost is from about 0.1% to about 0.2%

160. The formulation of any one of embodiments 118-151, wherein the concentration of bimatoprost is from about 0.005% to about 0.05%.

161. The formulation of any one of embodiments 118-151, wherein the concentration of bimatoprost is about 0.01%.

162. The formulation of any one of embodiments 118-151, wherein the concentration of bimatoprost is about 0.02%.

163. The formulation of any one of embodiments 118-151, wherein the concentration of bimatoprost is about 0.03%.

164. The formulation of any one of embodiments 118-151, wherein the concentration of bimatoprost is about 0.04%.

165. The formulation of any one of embodiments 118-151, wherein the concentration of bimatoprost is about 0.05%.

166. The formulation of any one of embodiments 118-165 for use in treating a condition selected from the group consisting of hypotrichosis of the eyelashes, hair loss of the eyebrows, hair loss of the scalp, and hypotrichosis associated with chemotherapy treatment regimens.

167. The formulation of any one of embodiments 118-166, for use in treating hypotrichosis of the eyelashes.

168. The formulation of any one of embodiments 118-166, for use in treating hair loss of the eyebrows.

169. The formulation of any one of embodiments 118-166, for use in treating hair loss of the scalp.

170. The formulation of any one of embodiments 118-166, for use in treating hypotrichosis associated with chemotherapy treatment regimens.

171. The formulation of any one of embodiments 118-170, wherein the alcohol is a $C_1$-$C_{20}$ alcohol.

172. The formulation of embodiment 171, wherein the alcohol is a $C_1$-$C_{10}$ alcohol.

173. The formulation of embodiment 172, wherein the alcohol is a $C_1$-$C_6$ alcohol.

174. The formulation of embodiment 173, wherein the alcohol is a $C_1$-$C_3$ alcohol.

175. The formulation of embodiment 172, wherein the alcohol is selected form the group of methanol, ethanol, 1-propanol, 1-butanol, 1-pentanol, propan-2-ol, 2-methylpropan-1-ol, butan-2-ol, 2-methylpropan-2-ol, 3-methylbutan-2-ol, 3-methylbutan-1-ol, 2-methylbutan-1-ol and 2-methylbutan-2-ol, pentan-3-ol, 2-methylpentan-2-ol, 2-methylpentan-3-ol, 4-methylpentan-2-ol, 4-methylpentan-1-ol, 2-methylpentan-1-ol, 3-methylpentan-1-ol, 3-methylpentan-2-ol, 3-methylpentan-3-ol, hexan-2-ol, hexan-3-ol, 2-methylhexan-1-ol, 2-methylhexan-2-ol, 2-methylhexan-3-ol, 5-methylhexan-3-ol, 5-methylhexan-2-ol, 5-methylhexan-1-ol, 3-methylhexan-1-ol, 3-methylhexan-2-ol, 3-methylhexan-3-ol, 4-methylhexan-3-ol, 4-methylhexan-2-ol, and 4-methylhexan-1-ol.

176. The formulation of embodiment 175, wherein the alcohol is selected form the group of ethanol, 1-propanol, 2-propanol and 1-butanol.

177. The formulation of embodiment 176, wherein the alcohol is ethanol.

178. The formulation of any one of embodiments 118-177, wherein the oil is a plant oil.

179. The formulation of any one of embodiments 118-177, wherein the oil is an animal oil.

180. The formulation of any one of embodiments 118-177, wherein the oil is a petroleum based oil.

181. The formulation of any one of embodiments 118-177, wherein the oil is not a plant or animal based oil.

182. The formulation of any one of embodiments 118-177, wherein the oil is selected from the group consisting of castor oil, avocado oil, jojoba oil, olive oil, rosemary oil, tea tree oil, sweet almond oil, and vitamin E.

183. The formulation of any one of embodiments 118-177, wherein the oil is selected from the group consisting of lavendar essential oil, cedar wood essential oil, thyme essential oil, clary sage essential oil, rosemary essential oil, polygonum multiflorum, castor oil, jojoba oil, avocado oil, olive oil, sweet almond oil, vitamin E.

184. The formulation of any one of embodiments 118-177, wherein two or more oils are used selected from the group consisting of avocado oil, olive oil, sweet almond oil, castor oil, rosemary oil, tea tree oil, jojoba oil, and vitamin E.

185. The formulation of any one of embodiments 118-184, wherein the formulation is applied once every 7 days.

186. The formulation of any one of embodiments 118-184, wherein the formulation is applied once every 2 days.

187. The formulation of any one of embodiments 118-184, wherein the formulation is applied once per day.

188. The formulation of any one of embodiments 118-184, wherein the formulation is applied twice per day.

189. The formulation of any one of embodiments 118-184, wherein the formulation is applied three times per day.

190. The formulation of any one of embodiments 118-184, wherein the formulation is applied to an area of skin containing at least one hair follicle.

191. The formulation of any one of embodiments 118-184, wherein the formulation is applied to an area selected from the group consisting of upper eyelid margin, eyebrows and the scalp.

192. The formulation of embodiment any one of embodiments 118-184, wherein the formulation is applied to an area of skin selected from the group consisting of the face, the scalp and the body.

193. The formulation of embodiment 192, wherein the formulation is applied to the face.

194. The formulation of any one of embodiments 118-184, wherein the formulation is applied to at least one eyelid margin.

195. The formulation of embodiment 194, wherein the formulation is applied to at least one upper eyelid margin.

196. The formulation of any one of embodiments 118-195, wherein the formulation elongates eyelash hairs by daily application over a period of 60 days.

197. The formulation of any one of embodiments 118-196, wherein the formulation is applied by a multi-use applicator.

198. The formulation of embodiment 118, wherein the alcohol is ethanol, and the oil is a combination of castor oil and jojoba oil.

199. The formulation of embodiment 118, wherein the formulation comprises about 0.02% w/v bimatoprost, about 1% v/v ethanol, about 3% v/v castor oil, about 71.6% v/v jojoba oil, about 24% v/v sweet almond oil, and about 0.4% v/v Vitamin E.

200. The formulation of embodiment 118, wherein the formulation comprises 0.3% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil and 0.5% v/v Vitamin E.

201. The formulation of embodiment 118, wherein the formulation comprises 0.1% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E.

202. The formulation of embodiment 118, wherein the formulation comprises 0.02%-0.03% w/v bimatoprost, about 1% v/v ethanol, about 3% v/v castor oil, and about 70-96% v/v jojoba oil.

203. The formulation of embodiment 118, wherein the concentration of bimatoprost is 0.02%;
the formulation is delivered to at least one upper eyelid margin;
the formulation is delivered with a multi-use applicator; and
the formulation results in equal or greater eyelash growth when compared to a
water-based formulation with a concentration of bimatoprost of 0.03%.

204. The formulation of embodiment 203, wherein the water-based formulation is applied with a single use applicator.

205. The formulation of embodiment 203, wherein the water-based formulation is applied with a brush contacting the eyelashes.

206. In one embodiment is a method for use in treating a condition selected from the group consisting of hypotrichosis of the eyelashes, hair loss of the eyebrows, hair loss of the scalp, and hypotrichosis associated with chemotherapy treatment regimens, comprising administrating to the patient a formulation comprised of:
at least one eicosanoid;
at least one oil; and
at least one alcohol; wherein
the formulation is substantially free of water; and
the formulation is substantially free of preservatives.

207. The method of embodiment 206, wherein the concentration of eicosanoid is from about 0.001% to about 5.0%.

208. The method of embodiment 206, wherein the concentration of eicosanoid is from about 0.01% to about 3.0%.

209. The method of embodiment 206, wherein the concentration of eicosanoid is from about 0.1% to about 0.3%.

210. The method of embodiment 206, wherein the concentration of eicosanoid is from about 0.01% to about 0.05%.

211. The method of any one of embodiments 206-210, wherein the eicosanoid is a prostanoid, leukotriene, lipoxin, resolvin, or eoxin.

212. The method of embodiment 211, wherein the eicosanoid is a prostanoid.

213. The method of embodiment 212, wherein the eicosanoid is a prostanoid selected from prostaglandin $F_{2\alpha}$, dinoprost, latanoprost, bimatoprost, travoprost, carboprost, and tafluprost.

214. The method of embodiment 213, wherein the prostanoid is bimatoprost.

215. The method of embodiment 213, wherein the prostanoid is prostaglandin $F_{2\alpha}$.

216. The method of embodiment 213, wherein the prostanoid is dinoprost.

217. The method of embodiment 213, wherein the prostanoid is latanoprost.

218. The method of embodiment 213, wherein the prostanoid is travoprost.

219. The method of embodiment 213, wherein the prostanoid is carboprost.

220. The method of embodiment 213, wherein the prostanoid is tafluprost.

221. In one embodiment is a method for use in treating a condition selected from the group consisting of hypotrichosis of the eyelashes, hair loss of the eyebrows, hair loss of the scalp, and hypotrichosis associated with chemotherapy treatment regimens, comprising administrating to the patient a formulation comprised of:
  bimatoprost;
  at least one oil; and
  at least one alcohol; wherein
  the formulation is substantially free of water; and
  the formulation is substantially free of preservatives.

222. The method of any one of embodiments 206-221, wherein the concentration of oil is from about 0.1% to about 99.0%.

223. The method of any one of embodiments 206-221, wherein the concentration of oil is from about 50.0% to about 99.0%.

224. The method of any one of embodiments 206-221, wherein the concentration of oil is from about 40.0% to about 50.0%.

225. The method of any one of embodiments 206-221, wherein the concentration of oil is from about 50.1% to about 60.0%.

226. The method of any one of embodiments 206-221, wherein the concentration of oil is from about 60.1% to about 70.0%.

227. The method of any one of embodiments 206-221, wherein the concentration of oil is from about 70.1% to about 80.0%.

228. The method of any one of embodiments 206-221, wherein the concentration of oil is from about 80.1% to about 90.0%.

229. The method of any one of embodiments 206-221, wherein the concentration of oil is from about 90.1% to about 99.0%.

230. The method of any one of embodiments 206-221, wherein the concentration of oil is from about 40.0% to about 55.0%.

231. The method of any one of embodiments 206-221, wherein the concentration of oil is from about 55.1% to about 70.0%.

232. The method of any one of embodiments 206-221, wherein the concentration of oil is from about 70.1% to about 85.0%.

233. The method of any one of embodiments 206-221, wherein the concentration of oil is from about 85.1% to about 99.0%.

234. The method of any one of embodiments 206-221, wherein the concentration of oil is about 93%.

235. The method of any one of embodiments 206-221, wherein the concentration of oil is about 95%.

236. The method of any one of embodiments 206-221, wherein the concentration of oil is about 97%.

237. The method of any one of embodiments 206-221, wherein the concentration of oil is about 99%.

238. The method of any one of embodiments 206-237, wherein the concentration of alcohol is from about 0.1% to about 50.0%.

239. The method of any one of embodiments 206-237, wherein the concentration of alcohol is from about 0.1% to about 20.0%.

240. The method of any one of embodiments 206-237, wherein the concentration of alcohol is from about 1.0% to about 15.0%.

241. The method of any one of embodiments 206-237, wherein the concentration of alcohol is from about 1.0% to about 10.0%.

242. The method of any one of embodiments 206-237, wherein the concentration of alcohol is from about 3.0% to about 10.0%.

243. The method of any one of embodiments 206-237, wherein the concentration of alcohol is from about 1.0% to about 5.0%.

244. The method of any one of embodiments 206-237, wherein the concentration of alcohol is from about 3.0% to about 8.0%.

245. The method of any one of embodiments 206-237, wherein the concentration of alcohol is from about 3.0% to about 5.0%.

246. The method of any one of embodiments 206-245, wherein substantially free of water is defined as less than 5.0%.

247. The method of any one of embodiments 206-245, wherein substantially free of water is defined as less than 2.0%.

248. The method of any one of embodiments 206-245, wherein substantially free of water is defined as less than 1.0%.

249. The method of any one of embodiments 206-245, wherein substantially free of water is defined as less than 0.5%.

250. The method of any one of embodiments 206-245, wherein substantially free of water is defined as less than 0.1%.

251. The method of any one of embodiments 206-245, wherein substantially free of water is defined as less than 0.05%.

252. The method of any one of embodiments 206-245, wherein substantially free of water is defined as less than 0.01%.

253. The method of any one of embodiments 206-245, wherein substantially free of water is defined as less than 0.005%.

254. The method of any one of embodiments 206-245, wherein substantially free of water is defined as less than 0.001%.

255. The method of any one of embodiments 206-245, wherein substantially free of preservative is defined as less than 5.0%.

256. The method of any one of embodiments 206-245, wherein substantially free of preservative is defined as less than 2.0%.

257. The method of any one of embodiments 206-245, wherein substantially free of preservative is defined as less than 1.0%.

258. The method of any one of embodiments 206-245, wherein substantially free of preservative is defined as less than 0.5%.

259. The method of any one of embodiments 206-245, wherein substantially free of preservative is defined as less than 0.1%.

260. The method of any one of embodiments 206-245, wherein substantially free of preservative is defined as less than 0.05%.

261. The method of any one of embodiments 206-245, wherein substantially free of preservative is defined as less than 0.01%.

262. The method of any one of embodiments 206-245, wherein substantially free of preservative is defined as less than 0.005%.

263. The method of any one of embodiments 206-245, wherein substantially free of preservative is defined as less than 0.001%.

264. The method of embodiment 221, wherein the concentration of bimatoprost is from about 0.001% to about 5.0%.

265. The method of embodiment 221, wherein the concentration of bimatoprost is from about 0.01% to about 3.0%.

266. The method of embodiment 221, wherein the concentration of bimatoprost is from about 0.01% to about 1.0%.

267. The method of embodiment 221, wherein the concentration of bimatoprost is from about 0.01% to about 0.5%.

268. The method of embodiment 221, wherein the concentration of bimatoprost is from about 0.02% to about 0.4%.

269. The method of embodiment 221, wherein the concentration of bimatoprost is from about 0.03% to about 0.3%.

270. The method of embodiment 221, wherein the concentration of bimatoprost is from about 0.1% to about 0.3%.

271. The method of embodiment 221, wherein the concentration of bimatoprost is from about 0.1% to about 0.2%

272. The method of embodiment 221, wherein the concentration of bimatoprost is from about 0.005% to about 0.05%.

273. The method of embodiment 221, wherein the concentration of bimatoprost is about 0.01%.

274. The method of embodiment 221, wherein the concentration of bimatoprost is about 0.02%.

275. The method of embodiment 221, wherein the concentration of bimatoprost is about 0.03%.

276. The method of embodiment 221, wherein the concentration of bimatoprost is about 0.04%.

277. The method of embodiment 221, wherein the concentration of bimatoprost is about 0.05%.

278. The method of any one of embodiments 206-277 for use in treating a condition selected from the group consisting of hypotrichosis of the eyelashes, hair loss of the eyebrows, hair loss of the scalp, and hypotrichosis associated with chemotherapy treatment regimens.

279. The method of any one of embodiments 206-278, for use in treating hypotrichosis of the eyelashes.

280. The method of any one of embodiments 206-278, for use in treating hair loss of the eyebrows.

281. The method of any one of embodiments 206-278, for use in treating hair loss of the scalp.

282. The method of any one of embodiments 206-278, for use in treating hypotrichosis associated with chemotherapy treatment regimens.

283. The method of any one of embodiments 206-282, wherein at least one alcohol is a $C_1$-$C_{20}$ alcohol.

284. The method of embodiment 283, wherein the alcohol is at least one $C_1$-$C_{10}$ alcohol.

285. The method of embodiment 284, wherein the alcohol is at least one $C_1$-$C_6$ alcohol.

286. The method of embodiment 285, wherein the alcohol is at least one $C_1$-$C_3$ alcohol.

287. The method of embodiment 284, wherein at least one alcohol is selected form the group of methanol, ethanol, 1-propanol, 1-butanol, 1-pentanol, propan-2-ol, 2-methylpropan-1-ol, butan-2-ol, 2-methylpropan-2-ol, 3-methylbutan-2-ol, 3-methylbutan-1-ol, 2-methylbutan-1-ol and 2-methylbutan-2-ol, pentan-3-ol, 2-methylpentan-2-ol, 2-methylpentan-3-ol, 4-methylpentan-2-ol, 4-methylpentan-1-ol, 2-methylpentan-1-ol, 3-methylpentan-1-ol, 3-methylpentan-2-ol, 3-methylpentan-3-ol, hexan-2-ol, hexan-3-ol, 2-methylhexan-1-ol, 2-methylhexan-2-ol, 2-methylhexan-3-ol, 5-methylhexan-3-ol, 5-methylhexan-2-ol, 5-methylhexan-1-ol, 3-methylhexan-1-ol, 3-methylhexan-2-ol, 3-methylhexan-3-ol, 4-methylhexan-3-ol, 4-methylhexan-2-ol, and 4-methylhexan-1-ol.

288. The method of embodiment 287, wherein at least one alcohol is selected form the group of ethanol, 1-propanol, 2-propanol and 1-butanol.

289. The method of embodiment 288, wherein the alcohol is ethanol.

290. The method of any one of embodiments 206-289, wherein at least one oil is a plant oil.

291. The method of any one of embodiments 206-289, wherein at least one oil is an animal oil.

292. The method of any one of embodiments 206-289, wherein at least one oil is a petroleum based oil.

293. The method of any one of embodiments 206-289, wherein at least one oil is not a plant or animal based oil.

294. The method of any one of embodiments 206-289, wherein at least one oil is selected from the group consisting of castor oil, avocado oil, jojoba oil, olive oil, rosemary oil, tea tree oil, sweet almond oil, and vitamin E.

295. The method of any one of embodiments 206-289, wherein at least one oil is selected from the group consisting of lavendar essential oil, cedar wood essential oil, thyme essential oil, clary sage essential oil, rosemary essential oil, polygonum multiflorum, castor oil, jojoba oil, avocado oil, olive oil, sweet almond oil, vitamin E.

296. The method of any one of embodiments 206-289, wherein at least two or more oils are selected from the group consisting of avocado oil, olive oil, sweet almond oil, castor oil, rosemary oil, tea tree oil, jojoba oil, and vitamin E.

297. The method of any one of embodiments 206-296, wherein the formulation is applied once every 7 days.

298. The method of any one of embodiments 206-296, wherein the formulation is applied once every 2 days.

299. The method of any one of embodiments 206-296, wherein the formulation is applied once per day.

300. The method of any one of embodiments 206-296, wherein the formulation is applied twice per day.

301. The method of any one of embodiments 206-296, wherein the formulation is applied three times per day.

302. The method of any one of embodiments 206-301, wherein the formulation is applied to an area of skin containing at least one hair follicle.

303. The method of any one of embodiments 206-301, wherein the formulation is applied to an area selected from the group consisting of upper eyelid margin, eyebrows and the scalp.

304. The method of embodiment any one of embodiments 206-301, wherein the formulation is applied to the face, the scalp or the body.

305. The method of embodiment 304, wherein the formulation is applied to the face.

306. The method of any one of embodiments 206-305, wherein the formulation is applied to at least one eyelid margin.

307. The method of embodiment 306, wherein the formulation is applied to at least one upper eyelid margin.

308. The method of any one of embodiments 206-307, wherein the formulation elongates eyelash hairs by daily application over a period of 60 days.

309. The method of any one of embodiments 206-308, wherein the formulation is applied by a multi-use applicator.

310. The method of any one of embodiments 206-309, wherein the alcohol is ethanol, and the oil is a combination of castor oil and jojoba oil.

311. The method of embodiment 221, wherein the formulation comprises about 0.02% w/v bimatoprost, about 1% v/v ethanol, about 3% v/v castor oil, about 71.6% v/v jojoba oil, about 24% v/v sweet almond oil, and about 0.4% v/v Vitamin E.

312. The method of embodiment 221, wherein the formulation comprises 0.3% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil and 0.5% v/v Vitamin E.

313. The method of embodiment 221, wherein the formulation comprises 0.1% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E.

314. The method of embodiment 221, wherein the formulation comprises 0.02%-0.03% w/v bimatoprost, about 1% v/v ethanol, about 3% v/v castor oil, and about 70-96% v/v jojoba oil.

315. The method of embodiment 221, wherein
the concentration of bimatoprost is 0.02%;
the formulation is delivered to at least one upper eyelid margin;
the formulation is delivered with a multi-use applicator; and
the formulation results in equal or greater eyelash growth when compared to a water-based formulation with a concentration of bimatoprost of 0.03%.

316. The method of embodiment 315, wherein the comparison water-based formulation is applied with a single use applicator.

317. The method of embodiment 315, wherein the comparison water-based formulation is applied with a brush contacting the eyelashes.

318. In one embodiment is a method for use in treating a condition selected from the group consisting of hypotrichosis of the eyelashes, hair loss of the eyebrows, hair loss of the scalp, and hypotrichosis associated with chemotherapy treatment regimens, comprising administrating to the patient a formulation consisting essentially of:
bimatoprost;
at least one oil; and
at least one alcohol; wherein
the formulation is substantially free of water; and
the formulation is substantially free of preservatives.

319. The method of embodiment 318, wherein the concentration of oil is from about 0.1% to about 99.0%.

320. The method of embodiment 318, wherein the concentration of oil is from about 50.0% to about 99.0%.

321. The method of embodiment 318, wherein the concentration of oil is from about 40.0% to about 50.0%.

322. The method of embodiment 318, wherein the concentration of oil is from about 50.0% to about 60.0%.

323. The method of embodiment 318, wherein the concentration of oil is from about 60.0% to about 70.0%.

324. The method of embodiment 318, wherein the concentration of oil is from about 70.0% to about 80.0%.

325. The method of embodiment 318, wherein the concentration of oil is from about 80.0% to about 90.0%.

326. The method of embodiment 318, wherein the concentration of oil is from about 90.0% to about 99.0%.

327. The method of embodiment 318, wherein the concentration of oil is from about 40.0% to about 55.0%.

328. The method of embodiment 318, wherein the concentration of oil is from about 55.0% to about 70.0%.

329. The method of embodiment 318, wherein the concentration of oil is from about 70.0% to about 85.0%.

330. The method of embodiment 318, wherein the concentration of oil is from about 85.0% to about 99.0%.

331. The method of embodiment 318, wherein the concentration of oil is about 93%.

332. The method of embodiment 318, wherein the concentration of oil is about 95%.

333. The method of embodiment 318, wherein the concentration of oil is about 97%.

334. The method of embodiment 318, wherein the concentration of oil is about 99%.

335. The method of any one of embodiments 318-334, wherein the concentration of alcohol is from about 0.1% to about 50.0%.

336. The method of any one of embodiments 318-334, wherein the concentration of alcohol is from about 0.1% to about 20.0%.

337. The method of any one of embodiments 318-334, wherein the concentration of alcohol is from about 1.0% to about 15.0%.

338. The method of any one of embodiments 318-334, wherein the concentration of alcohol is from about 1.0% to about 10.0%.

339. The method of any one of embodiments 318-334, wherein the concentration of alcohol is from about 3.0% to about 10.0%.

340. The method of any one of embodiments 318-334, wherein the concentration of alcohol is from about 1.0% to about 5.0%.

341. The method of any one of embodiments 318-334, wherein the concentration of alcohol is from about 3.0% to about 8.0%.

342. The method of any one of embodiments 318-334, wherein the concentration of alcohol is from about 3.0% to about 5.0%.

343. The method of any one of embodiments 318-342, wherein substantially free is defined as less than 5.0%.

344. The method of any one of embodiments 318-342, wherein substantially free is defined as less than 2.0%.

345. The method of any one of embodiments 318-342, wherein substantially free is defined as less than 1.0%.

346. The method of any one of embodiments 318-342, wherein substantially free is defined as less than 0.5%.

347. The method of any one of embodiments 318-342, wherein substantially free is defined as less than 0.1%.

348. The method of any one of embodiments 318-342, wherein substantially free is defined as less than 0.05%.

349. The method of any one of embodiments 318-342, wherein substantially free is defined as less than 0.01%.

350. The method of any one of embodiments 318-342, wherein substantially free is defined as less than 0.005%.

351. The method of any one of embodiments 318-342, wherein substantially free is defined as less than 0.001%.

352. The method of any one of embodiments 318-351, wherein the concentration of bimatoprost is from about 0.001% to about 5.0%.

353. The method of any one of embodiments 318-351, wherein the concentration of bimatoprost is from about 0.01% to about 3.0%.

354. The method of any one of embodiments 318-351, wherein the concentration of bimatoprost is from about 0.01% to about 1.0%.

355. The method of any one of embodiments 318-351, wherein the concentration of bimatoprost is from about 0.01% to about 0.5%.

356. The method of any one of embodiments 318-351, wherein the concentration of bimatoprost is from about 0.02% to about 0.4%.

357. The method of any one of embodiments 318-351, wherein the concentration of bimatoprost is from about 0.03% to about 0.3%.

358. The method of any one of embodiments 318-351, wherein the concentration of bimatoprost is from about 0.1% to about 0.3%.

359. The method of any one of embodiments 318-351, wherein the concentration of bimatoprost is from about 0.1% to about 0.2%

360. The method of any one of embodiments 318-351, wherein the concentration of bimatoprost is from about 0.005% to about 0.05%.

361. The method of any one of embodiments 318-351, wherein the concentration of bimatoprost is about 0.01%.

362. The method of any one of embodiments 318-351, wherein the concentration of bimatoprost is about 0.02%.

363. The method of any one of embodiments 318-351, wherein the concentration of bimatoprost is about 0.03%.

364. The method of any one of embodiments 318-351, wherein the concentration of bimatoprost is about 0.04%.

365. The method of any one of embodiments 318-351, wherein the concentration of bimatoprost is about 0.05%.

366. The method of any one of embodiments 318-365 for use in treating a condition selected from the group consisting of hypotrichosis of the eyelashes, hair loss of the eyebrows, hair loss of the scalp, and hypotrichosis associated with chemotherapy treatment regimens.

367. The method of any one of embodiments 318-366, for use in treating hypotrichosis of the eyelashes.

368. The method of any one of embodiments 318-366, for use in treating hair loss of the eyebrows.

369. The method of any one of embodiments 318-366, for use in treating hair loss of the scalp.

370. The method of any one of embodiments 318-366, for use in treating hypotrichosis associated with chemotherapy treatment regimens.

371. The method of any one of embodiments 318-370, wherein the alcohol is a $C_1$-$C_{20}$ alcohol.

372. The method of embodiment 371, wherein the alcohol is a $C_1$-$C_{10}$ alcohol.

373. The method of embodiment 372, wherein the alcohol is a $C_1$-$C_6$ alcohol.

374. The method of embodiment 373, wherein the alcohol is a $C_1$-$C_3$ alcohol.

375. The method of embodiment 373, wherein the alcohol is selected form the group of methanol, ethanol, 1-propanol, 1-butanol, 1-pentanol, propan-2-ol, 2-methylpropan-1-ol, butan-2-ol, 2-methylpropan-2-ol, 3-methylbutan-2-ol, 3-methylbutan-1-ol, 2-methylbutan-1-ol and 2-methylbutan-2-ol, pentan-3-ol, 2-methylpentan-2-ol, 2-methylpentan-3-ol, 4-methylpentan-2-ol, 4-methylpentan-1-ol, 2-methylpentan-1-ol, 3-methylpentan-1-ol, 3-methylpentan-2-ol, 3-methylpentan-3-ol, hexan-2-ol, hexan-3-ol, 2-methylhexan-1-ol, 2-methylhexan-2-ol, 2-methylhexan-3-ol, 5-methylhexan-3-ol, 5-methylhexan-2-ol, 5-methylhexan-1-ol, 3-methylhexan-1-ol, 3-methylhexan-2-ol, 3-methylhexan-3-ol, 4-methylhexan-3-ol, 4-methylhexan-2-ol, and 4-methylhexan-1-ol.

376. The method of embodiment 175, wherein the alcohol is selected form the group of ethanol, 1-propanol, 2-propanol and 1-butanol.

377. The method of embodiment 376, wherein the alcohol is ethanol.

378. The method of any one of embodiments 318-377, wherein the oil is a plant oil.

379. The method of any one of embodiments 318-377, wherein the oil is an animal oil.

380. The method of any one of embodiments 318-377, wherein the oil is a petroleum based oil.

381. The method of any one of embodiments 318-377, wherein the oil is not a plant or animal based oil.

382. The method of any one of embodiments 318-377, wherein the oil is selected from the group consisting of castor oil, avocado oil, jojoba oil, olive oil, rosemary oil, tea tree oil, sweet almond oil, and vitamin E.

383. The method of any one of embodiments 318-377, wherein the oil is selected from the group consisting of lavendar essential oil, cedar wood essential oil, thyme essential oil, clary sage essential oil, rosemary essential oil, polygonum multiflorum, castor oil, jojoba oil, avocado oil, olive oil, sweet almond oil, vitamin E.

384. The method of any one of embodiments 318-377, wherein two or more oils are used selected from the group consisting of avocado oil, olive oil, sweet almond oil, castor oil, rosemary oil, tea tree oil, jojoba oil, and vitamin E.

385. The method of any one of embodiments 318-384, wherein the formulation is applied once every 7 days.

386. The method of any one of embodiments 318-384, wherein the formulation is applied once every 2 days.

387. The method of any one of embodiments 318-384, wherein the formulation is applied once per day.

388. The method of any one of embodiments 318-384, wherein the formulation is applied twice per day.

389. The method of any one of embodiments 318-384, wherein the formulation is applied three times per day.

390. The method of any one of embodiments 318-384, wherein the formulation is applied to an area of skin containing at least one hair follicle.

391. The method of any one of embodiments 318-384, wherein the formulation is applied to an area selected from the group consisting of upper eyelid margin, eyebrows and the scalp.

392. The method of embodiment any one of embodiments 318-384, wherein the formulation is applied to an area of skin selected from the group consisting of the face, the scalp and the body.

393. The method of embodiment 392, wherein the formulation is applied to the face.

394. The method of any one of embodiments 318-384, wherein the formulation is applied to at least one eyelid margin.

395. The method of embodiment 394, wherein the formulation is applied to at least one upper eyelid margin.

396. The method of any one of embodiments 318-395, wherein the formulation elongates eyelash hairs by daily application over a period of 60 days.

397. The method of any one of embodiments 318-396, wherein the formulation is applied by a multi-use applicator.

398. The method of embodiment 318, wherein the alcohol is ethanol, and the oil is a combination of castor oil and jojoba oil.

399. The method of embodiment 318, wherein the formulation comprises about 0.02% w/v bimatoprost, about 1% v/v ethanol, about 3% v/v castor oil, about 71.6% v/v jojoba oil, about 24% v/v sweet almond oil, and about 0.4% v/v Vitamin E.

400. The method of embodiment 318, wherein the formulation comprises 0.3% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil and 0.5% v/v Vitamin E.

401. The method of embodiment 318, wherein the formulation comprises 0.1% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E.

402. The method of embodiment 318, wherein the formulation comprises 0.02%-0.03% w/v bimatoprost, about 1% v/v ethanol, about 3% v/v castor oil, and about 70-96% v/v jojoba oil.

403. A method of relieving dry eye by applying a formulation comprising at least one naturally occurring oil to the eyelid margin, wherein the formulation is substantially free of water and is free of preservatives.

404. The method of embodiment 403, wherein the concentration of the oil is from about 1% to about 99%.

405. The method of embodiment 403, wherein the concentration of the oil is from about 50% to about 99%.

406. The method of embodiment 403, wherein the concentration of the oil is from about 70% to about 99%.

407. The method of embodiment 403, wherein the concentration of the oil is from about 80% to about 99%.

408. The method of embodiment 403, wherein the concentration of the oil is from about 90% to about 99%.

409. The method of embodiment 403, wherein the concentration of the oil is from about 93% to about 99%.

410. The method of embodiment 403, wherein the concentration of the oil is from about 95% to about 99%.

411. The method of embodiment 403, wherein the concentration of the oil is from about 97% to about 99%.

412. The method of embodiment 403, wherein the concentration of the oil is from about 90% to about 97%.

413. The method of embodiment 403, wherein the concentration of the oil is from about 93% to about 98%.

414. The method of any one of embodiments 403-413, where the oil is linear or branched.

415. The method of any one of embodiments 403-413, where the oil is saturated or unsaturated.

416. The method of any one of embodiments 403-413, where the oil is substituted with one, two, or three substituents.

417. The method of any one of embodiments 403-413, where the oil is made up of 10 to 40 carbon atoms.

418. The method of embodiment 403 where the formulation is about 71.6% v/v jojoba oil, about 3% v/v castor oil, about 24% v/v sweet almond oil, and about 0.4% Vitamin E.

419. In one embodiment is a method of application whereby the formulation of any of embodiments 1-205 is delivered to the eyelid margin by a positive displacement device comprising a reservoir attached to a roller ball, brush, or felt tip device.

420. In one embodiment is a non-aqueous, non-preserved formulation for stimulating hair growth, comprising an eicosanoid, ethanol and an oil, wherein the eicosanoid is present in a concentration of about 0.01%-0.3% w/v and ethanol is present in a concentration of about 1%-7% v/v.

421. The formulation of embodiment 420 wherein the eicosanoid is bimatoprost and the oil is a plant oil.

422. The formulation of embodiment 420 wherein the plant oil is selected from the group consisting of lavendar essential oil, cedar wood essential oil, thyme essential oil, clary sage essential oil, rosemary essential oil, polygonum multiflorum, castor oil, jojoba oil, avocado oil, olive oil, sweet almond oil, vitamin E.

423. The formulation of embodiment 421 or 422, wherein formulation is for stimulating eyelash growth and comprises about 0.02-0.03% w/v bimatoprost.

424. The formulation of embodiment 423 comprising about 0.03% w/v bimatoprost, about 1% v/v ethanol, about 3% v/v castor oil and about 96% v/v jojoba oil.

425. The formulation of embodiment 422 comprising about 0.02% w/v bimatoprost, about 1% v/v ethanol, about 3% v/v castor oil, and about 71.6% v/v jojoba oil, about 24% v/v sweet almond oil, and about 0.4% v/v vitamin E.

426. The formulation of embodiment 421 or 422, wherein formulation is for stimulating scalp growth and comprises about 0.01%-0.3% w/v bimatoprost.

427. The formulation of embodiment 426 comprising 0.3% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil, 0.5% v/v Vitamin E.

428. The formulation of embodiment 421 or 422, wherein formulation is for stimulating eyebrow growth and comprises about 0.01%-0.3% w/v bimatoprost.

429. The formulation of embodiment 428 comprising 0.1% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E.

EXAMPLES

Example I

Bacterial and Mold Growth

Figure 2:
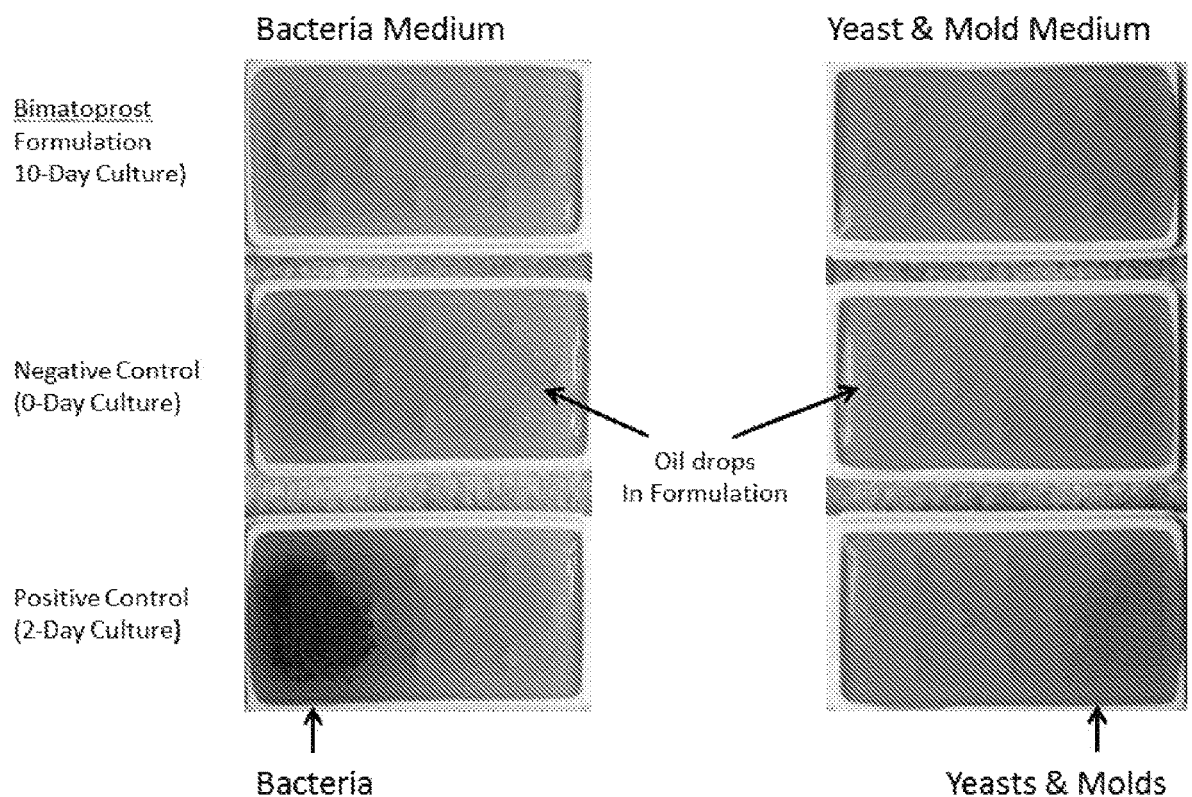
FIG. 2 shows the results of no bacterial and fungal growth on Formulation 3, Table 1 as described in Example I.

Test: (0.03% Bimatoprost anhydrous formulation) of the following 8 month old formulation:
0.03% w/v bimatoprost, 1% v/v ethanol, 3% v/v castor oil, and 96% v/v jojoba oil (Formulation 3, Table 1) was swiped on Microslides (LotionCraft, Cat #M-NUT/MAC)
Starting Date: Day 0
End Date: Day 10
Yellow side: tested for bacterial growth
Pink side: tested for yeast and molds
Procedure:
1) Swipe 0.03% Bimatoprost anhydrous formulation on both sides of pack #1 of Microslides, incubated for 10 days in room temperature
2) Negative control: swipe 0.03% Bimatoprost anhydrous formulation on both sides of pack #2 of Microslides, no incubation, took picture immediately.
3) Positive control for microbial growth: inoculated household microbes on both sides of pack #3 of Microslides, incubated for two days when pictures were taken.
Observe for microbial growth every day and take picture on Day 10 with controls.
Results: photos on Day 10, see FIG. 2.
Conclusion: no bacteria, yeast or mold was found on tested 0.03% Bimatoprost anhydrous formulation or the negative control.

Example II

A 52-year old female with short and sparsely dense eyelashes applied the Formulation 3 (Table I) consisting of 0.03% w/v bimatoprost, 96% v/v jojoba oil, 3% v/v castor oil, 1% v/v ethanol once daily to the upper eyelid margin. This was achieved by using a pen-like cylindrical reservoir fitted with a felt/fiber tip (see FIG. 1). The bimatoprost formulation was applied to the upper eyelid margin by a single directed motion. Following 8 weeks of daily treatment, the eyelashes increased in length by approximately 50% and the eyelash population was distinctly denser.

Example III

Figure 3:
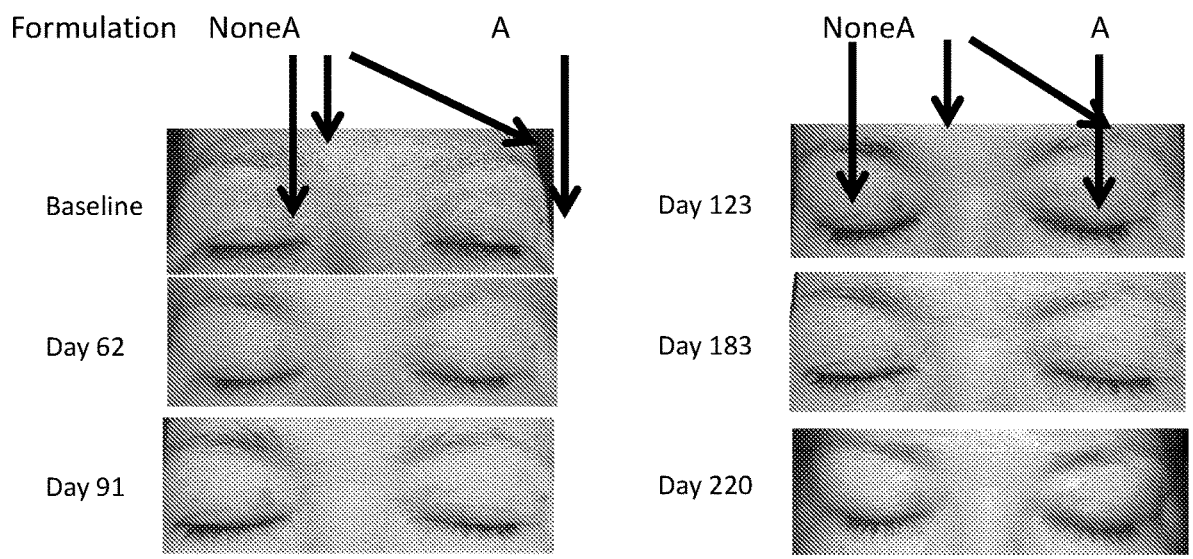
FIG. 3 shows the results of the growth of right eyelash and left and right eyebrows using Formulation 13, Table 2 as described in Example III.

A 57-year old female with short and sparsely dense eyelashes and eyebrows applied the Formulation 13 (Table 2) consisting of 0.02% w/v bimatoprost, 71.6% v/v jojoba oil, 24% v/v sweet almond oil, 3% v/v castor oil, 1% v/v ethanol and 0.4% v/v vitamin E ("Formulation NoneA) once daily to the right upper eyelid margin and to the left and right eyebrows. This was achieved by using a pen-like cylindrical reservoir fitted with a felt/fiber tip (see FIG. 1). As comparison, an aqueous eyelash growth product ("Formulation A") with 0.03% w/v bimatoprost currently on the market was applied on the left upper eyelid margin according to the product instruction. The eyelash became darker and longer after 123 days of daily bimatoprost treatment and the eyebrow became darker and longer after 91 days of daily bimatoprost treatment (see FIG. 3). There was no obvious difference on eyelash growth between "Formulation NoneA with 0.02% bimatoprost and Formulation A with 0.03% bimatoprost.

Example IV

Figure 4:
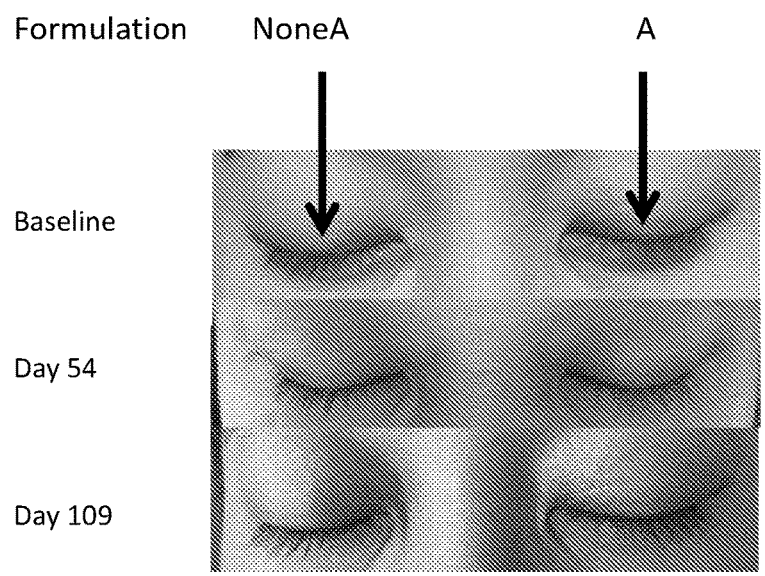
FIG. 4 shows the results of the growth of right eyelash using Formulation 13, Table 2 as described in Example IV.

A 45-year old female with normal length and dense eyelashes applied the Formulation 13 (Table 2) consisting of 0.02% w/v bimatoprost, 71.6% v/v jojoba oil, 24% v/v sweet almond oil, 3% v/v castor oil, 1% v/v ethanol and 0.4% v/v vitamin E ("Formulation NoneA") once daily to the right upper eyelid margin. This was achieved by using a pen-like cylindrical reservoir fitted with a felt/fiber tip (see FIG. 1). As comparison, an aqueous eyelash growth product ("Formulation A") with 0.03% w/v bimatoprost currently on the market was applied on the left upper eyelid margin according to the product instruction. The eyelash became darker and longer after 109 days of daily bimatoprost treatment (see FIG. 4). There was no obvious difference on eyelash growth between "Formulation NoneA with 0.02% bimatoprost and Formulation A with 0.03% bimatoprost.

Example V

A Caucasian female who has undergone chemotherapy experiences hypotrichosis of the eyelashes. The patient applies once daily the Formulation 13 (Table II) of 0.02% w/v bimatoprost, 1% v/v ethanol, 3% v/v castor oil, 71.6% v/v jojoba oil, 24% v/v sweet almond oil, and 0.4% v/v Vitamin E. After 60 days of daily application, the patient's eyelashes are thicker, longer and darker than prior to treatment.

Example VI

A 32 year old Hispanic male suffers from alopecia areata and begins losing hair. The patient applies once daily the Formulation 31 (Table IV) of 0.3% w/v bimatoprost, 7% v/v ethanol, 3% v/v castor oil, 64.5% v/v jojoba oil, 12% v/v olive oil, 12% sweet almond oil, 0.5% v/v Rosemary oil, 0.5% v/v tea tree oil, 0.5% v/v Vitamin E. After applying the formulation the patient experiences new hair growth on his scalp and his alopecia areata symptoms improve.

Example VII

A 51 year old Caucasian female notices that her eyebrows are thinning. The 51 year old Caucasian female applies the Formulation 25 (Table III) of 0.1% w/v bimatoprost, 3% v/v ethanol, 3% v/v castor oil, 68.5% v/v jojoba oil, 8% v/v avocado oil, 8% v/v olive oil, 8% v/v sweet almond oil, 0.5% v/v rosemary oil, 0.5% v/v tea tree oil, 0.5% v/v Vitamin E. After 60 days of twice daily application, the patient's eyebrow increase in density, length, are thicker and denser.

Example VIII

An Asian female diagnosed with dry eye disease applies the Formulation 3 (Table V) consisting of 0.03% w/v bimatoprost, 96% v/v jojoba oil, 3% v/v castor oil, 1% v/v ethanol once daily to the upper eyelid margin. This is achieved by using a pen-like cylindrical reservoir fitted with a felt/fiber tip (see FIG. 1) once daily before bed time. After 2-3 months daily use at night before bed time on both eyes, the dry eye symptoms were relieved. The dry eye symptoms came back on discontinuing use of the formulation for a few months.

Example IX

An Asian female diagnosed with dry eye disease applied formulation 34 of Table VI consisting of 71.6% v/v jojoba oil, 3% v/v castor oil, 24% v/v sweet almond oil, 0.4% Vitamin E oil once daily to the upper and lower eyelid margins. This was achieved by using a pen-like cylindrical reservoir fitted with a felt/fiber tip (see FIG. 1). After one month daily use at night before sleep on both eyes, the user reported that the formulation provided relief of symptoms associated with dry eye. Additionally, the user reported that compared to eye drops, this method of treatment was preferred due to the absence of any stinging sensation commonly associated with application of eye drops. The user also reported a superior level of relief of dry-eye symptoms as compared to a prior course of therapy comprising an eye drop formulation containing 0.1% fluorometholone and eye drop formulation containing 0.1% sodium hyaluronate [active: fluorometholone 0.1%. preservative: benzalkonium chloride 0.004%. Inactives: edetate disodium; polysorbate 80; polyvinyl alcohol 1.4%; purified water; sodium chloride; sodium phosphate, dibasic; sodium phosphate, monobasic; and sodium hydroxide to adjust pH. FML® suspension is formulated with a pH from 6.2 to 7.5. It has an osmolality range of 290-350 mOsm/kg and active: sodium hyaluronate 0.1%. Inactives: e-Aminocaproic acid, disodium edetate, benzalkonium chloride, sodium chloride, potassium chloride, pH adjuster. pH from 6.0 to 7.0. Osmolality 0.9-1.1]

The patient reported a lack of stinging sensation immediately after use, with no stinging sensation from the test formulation. Additionally, the patient reported the eyes feel more moisturized after using the test formulation.

Example X

A Caucasian female presenting with dry eye disease symptomology applied formulation 34 of Table VI consisting of 71.6% v/v jojoba oil, 3% v/v castor oil, 24% v/v sweet almond oil, 0.4% Vitamin E oil once daily before bedtime to the upper eyelid margins. This was achieved by using a pen-like cylindrical reservoir fitted with a felt/fiber tip (see FIG. 1). This formulation was described as providing relief of symptoms for 1-5 hours.

Example XI

A Caucasian female presenting with dry eye disease symptomology applied formulation 34 of Table VI consisting of 71.6% v/v jojoba oil, 3% v/v castor oil, 24% v/v sweet almond oil, 0.4% Vitamin E oil once daily before sleep to the upper eyelid margins. The female has experienced relief of symptoms for a few hours in a day.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of relieving dry eye by applying a formulation comprising at least one naturally occurring oil to the eyelid margin, wherein the formulation is free of preservatives and comprises less than 5.0% of water.

2. The method of claim 1, wherein the concentration of the oil is from about 1% to about 99%.

3. The method of claim 1, wherein the concentration of the oil is from about 50% to about 99%.

4. The method of claim 1, wherein the concentration of the oil is from about 70% to about 99%.

5. The method of claim 1, wherein the concentration of the oil is from about 80% to about 99%.

6. The method of claim 1, wherein the concentration of the oil is from about 90% to about 99%.

7. The method of claim 1, wherein the concentration of the oil is from about 93% to about 99%.

8. The method of claim 1, wherein the concentration of the oil is from about 95% to about 99%.

9. The method of claim 1, wherein the concentration of the oil is from about 97% to about 99%.

10. The method of claim 1, wherein the concentration of the oil is from about 90% to about 97%.

11. The method of claim 1, wherein the concentration of the oil is from about 93% to about 98%.

12. The method of claim 1, where the chemical structure of the oil is linear or branched.

13. The method of claim 1, where the chemical structure of the oil is saturated or unsaturated.

14. The method of claim 1, where the chemical structure of the oil is substituted with one, two, or three substituents.

15. The method of claim 1, where the chemical structure of the oil is made up of 10 to 40 carbon atoms.

16. The method of claim 1, where the at least one naturally occurring oil is selected from jojoba oil, sweet almond oil, soybean oil, or castor oil.

17. The method of claim 1, where the at least one naturally occurring oil is selected from jojoba oil, or castor oil.

18. The method of claim 1, where the formulation is about 71.6% v/v jojoba oil, about 3% v/v castor oil, about 24% v/v sweet almond oil, and about 0.4% Vitamin E oil.

* * * * *